United States Patent
Lorey et al.

(10) Patent No.: US 10,308,694 B2
(45) Date of Patent: Jun. 4, 2019

(54) PRONGF MUTANTS AND USES THEREOF IN THE PRODUCTION OF BETA-NGF

(71) Applicants: Susan Lorey, Halle/Saale (DE); Bernhard Janowski, Halle/Saale (DE); Heiko Pultke, Halle/Saale (DE); Daniela Kathmann, Halle/Saale (DE); Antje Parthier, Halle/Saale (DE); Andreas Anton, Halle/Saale (DE)

(72) Inventors: Susan Lorey, Halle/Saale (DE); Bernhard Janowski, Halle/Saale (DE); Heiko Pultke, Halle/Saale (DE); Daniela Kathmann, Halle/Saale (DE); Antje Parthier, Halle/Saale (DE); Andreas Anton, Halle/Saale (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 14/978,407

(22) Filed: Dec. 22, 2015

(65) Prior Publication Data

US 2016/0244496 A1    Aug. 25, 2016

Related U.S. Application Data

(62) Division of application No. 14/366,460, filed as application No. PCT/EP2012/076251 on Dec. 19, 2012, now Pat. No. 9,617,322.

(30) Foreign Application Priority Data

Dec. 19, 2011  (EP) .................................. 11194208

(51) Int. Cl.
 *C07K 14/48*  (2006.01)
(52) U.S. Cl.
 CPC .................... *C07K 14/48* (2013.01)
(58) Field of Classification Search
 CPC .................. C07K 14/48; C12N 2501/13
 See application file for complete search history.

(56) References Cited

U.S. PATENT DOCUMENTS

| | | |
|---|---|---|
| 7,507,799 B2 | 3/2009 | Hempstead et al. |
| 2008/0050776 A1 | 2/2008 | Neet |
| 2010/0203589 A1 | 8/2010 | Rattenholl et al. |
| 2015/0087020 A1 | 3/2015 | Lorey |

FOREIGN PATENT DOCUMENTS

| | | |
|---|---|---|
| EP | 2135951 A1 | 12/2009 |
| EP | 2672984 A1 | 12/2013 |
| JP | 2002-527062 A | 8/2002 |
| WO | 2005061716 A1 | 7/2005 |
| WO | 2005068498 A2 | 7/2005 |
| WO | 2013092776 A1 | 6/2013 |

OTHER PUBLICATIONS

English Translation of Chinese Office Action for CN 201280062855.6 dated Jun. 4, 2015.
Definition: Nerve growth factor beta polypeptide, partial (bombycilla garrulus), Database DDBJ/EMBL/GenBank (online), Accessin No. ACF32193, Jul. 14, 2008 uploaded, (retrieved on Jun. 17, 2015), http://www.ncbi.nlm.nih.gov/protein/ACf32193.
Definition: Nerve growth factor beta polypeptide, partial (Platystemon megacephalum), Database DDBJ/EMBL/GenBank (online), Accessin No. ACY72443, May 6, 2010 uploaded, (retrieved on Jun. 17, 2015), http://www.ncbi.nlm.nih.gov/protein/ACY72443.
Abstract in English for JPH06-327489, date of publication Nov. 29, 1994.
NGF protein, partial [*Homo sapiens*], GenBank: AAH32517.2.
Pagadala, Promila C. et al., "Construction of a mutated pro-nerve growth factor resistant to degradation and suitable or biophysical and cellular utilization" PNAS, vol. 103, No. 47, Nov. 21, 2006.
Merck & Co., Inc., "The Merck index" Merck Research Laboratories, 1996, Ed. 12th, pp . 9930.
Notice of Opposition to a European Patent Patent No. EP2672984.
Clewes et al., "Human ProNFG: biological effects and binding profiles at TrkA, P75NTR and sortilin" Journal of Neurochemistry, 2008 (107), 1124-1135 (12 pgs.).

*Primary Examiner* — Robert C Hayes

(74) *Attorney, Agent, or Firm* — Steven M. Shape; Dennemeyer & Associates, LLC

(57) ABSTRACT

The present invention relates to a proNGF mutant and to uses thereof, in particular the use of a proNGF mutant for producing human beta-NGF. The present invention discloses a method of preparing a biologically active human beta-NGF from an inactive insoluble proNGF mutant. A proNGF mutant of the invention is substituted by any amino acid but not Arg or Lys at the native protease cleavage site $R^1SK^3R^4$ at least at positions $R^1$ and $K^3$ corresponding to positions 101 and 103 of the human wildtype proNGF sequence.

26 Claims, 5 Drawing Sheets

Specification includes a Sequence Listing.

Figure 1

Figure 1a. Sequence of the human proNGF (SEQ ID NO: 1)

MEPHSESNVPAGHTIPQVHWTKLQHSLDTALRRARSAPAAAIAARVAGQTRNITVDPRLFKKRRLRSPRVLFST
QPPREAADTQDLDFEVGGAAPFNRTH*RSKR*SSSHPIFHRGEFSVCDSVSVWVGDKTTATDIKGKEVMVLGEVNIN
NSVFKQYFFETKCRDPNPVDSGCRGIDSKHWNSYCTTTHTFVKALTMDGKQAAWRFIRIDTACVCVLSRKAVR

Figure 1b. Sequence of a proNGF mutant of the invention (SEQ ID NO: 2)

MEPHSESNVPAGHTIPQVHWTKLQHSLDTALRRARSAPAAAIAARVAGQTRNITVDPRLFKKRRLRSPRVLFST
QPPREAADTQDLDFEVGGAAPFNRTH*VSXR*SSSHPIFHRGEFSVCDSVSVWVGDKTTATDIKGKEVMVLGEVNI
NNSVFKQYFFETKCRDPNPVDSGCRGIDSKHWNSYCTTTHTFVKALTMDGKQAAWRFIRIDTACVCVLSRKAVR

Figure 1c. Sequence of a proNGF mutant of the invention (SEQ ID NO: 3)

MEPHSESNVPAGHTIPQVHWTKLQHSLDTALRRARSAPAAAIAARVAGQTRNITVDPRLFKKRRLRSPRVLFST
QPPREAADTQDLDFEVGGAAPFNRTH*XSXR*SSSHPIFHRGEFSVCDSVSVWVGDKTTATDIKGKEVMVLGEVNIN
NSVFKQYFFETKCRDPNPVDSGCRGIDSKHWNSYCTTTHTFVKALTMDGKQAAWRFIRIDTACVCVLSRKAVR

Figure 1d. Sequence of a proNGF mutant of the invention (SEQ ID NO: 4)

MEPHSESNVPAGHTIPQVHWTKLQHSLDTALRRARSAPAAAIAARVAGQTRNITVDPRLFKKRRLRSPRVLFST
QPPREAADTQDLDFEVGGAAPFNRTH*XSAR*SSSHPIFHRGEFSVCDSVSVWVGDKTTATDIKGKEVMVLGEVNIN
NSVFKQYFFETKCRDPNPVDSGCRGIDSKHWNSYCTTTHTFVKALTMDGKQAAWRFIRIDTACVCVLSRKAVR

Figure 1e. Sequence of proNGF mutant SP174-101 (SEQ ID NO: 5)

MEPHSESNVPAGHTIPQVHWTKLQHSLDTALRRARSAPAAAIAARVAGQTRNITVDPRLFKKRRLRSPRVLFST
QPPREAADTQDLDFEVGGAAPFNRTH*VSAR*SSSHPIFHRGEFSVCDSVSVWVGDKTTATDIKGKEVMVLGEVNIN
NSVFKQYFFETKCRDPNPVDSGCRGIDSKHWNSYCTTTHTFVKALTMDGKQAAWRFIRIDTACVCVLSRKAVR

Figure 1f. Sequence of a proNGF mutant of the invention (SEQ ID NO: 7)

MEPHSESNVPAGHTIPQVHWTKLQHSLDTALRRARSAPAAAIAARVAGQTRNITVDPRLFKKRRLRSPRVLFST
QPPREAADTQDLDFEVGGAAPFNRTH*XXXR*SSSHPIFHRGEFSVCDSVSVWVGDKTTATDIKGKEVMVLGEVNIN
NSVFKQYFFETKCRDPNPVDSGCRGIDSKHWNSYCTTTHTFVKALTMDGKQAAWRFIRIDTACVCVLSRKAVR

Figure 1g. Sequence of a proNGF mutant of the invention (SEQ ID NO: 8)

MEPHSESNVPAGHTIPQVHWTKLQHSLDTALRRARSAPAAAIAARVAGQTRNITVDPRLFKKRRLRSPRVLFST
QPPREAADTQDLDFEVGGAAPFNRTH*VXAR*SSSHPIFHRGEFSVCDSVSVWVGDKTTATDIKGKEVMVLGEVNI
NNSVFKQYFFETKCRDPNPVDSGCRGIDSKHWNSYCTTTHTFVKALTMDGKQAAWRFIRIDTACVCVLSRKAVR

Figure 1h. Further protease cleavage sites

RXKR (SEQ ID NO: 6); RSKR (SEQ ID NO: 9); VSXR (SEQ ID NO: 10); XSXR (SEQ ID NO: 11); XSAR (SEQ ID NO: 12); VSAR (SEQ ID NO: 13); XXXR (SEQ ID NO: 14); VXAR (SEQ ID NO: 15).

Figure 2. Processing of proNGF or proNGF mutants to beta-NGF
Figure 2a. Processing of wild-type proNGF
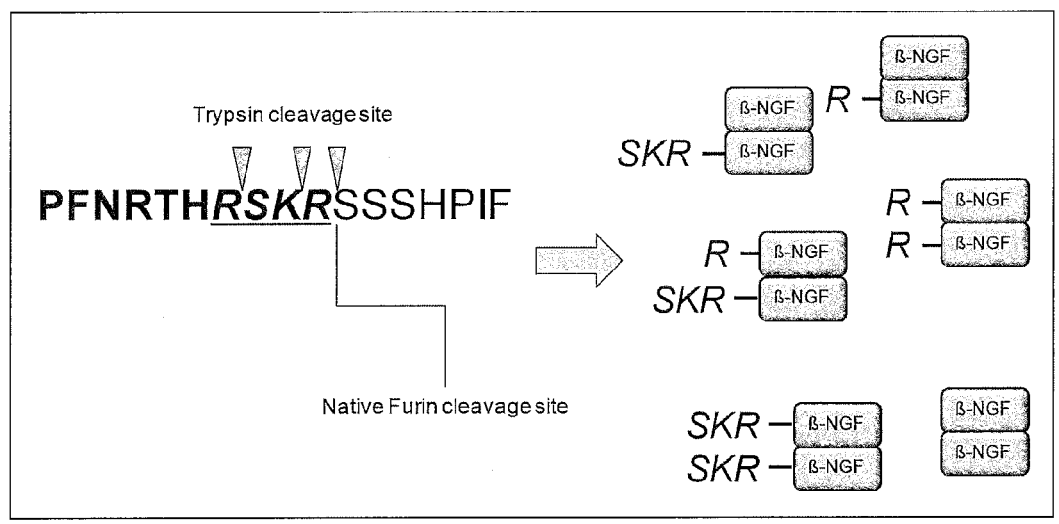
Figure 2b. Processing of proNGF mutant SP174-101 (SEQ ID NO: 5)
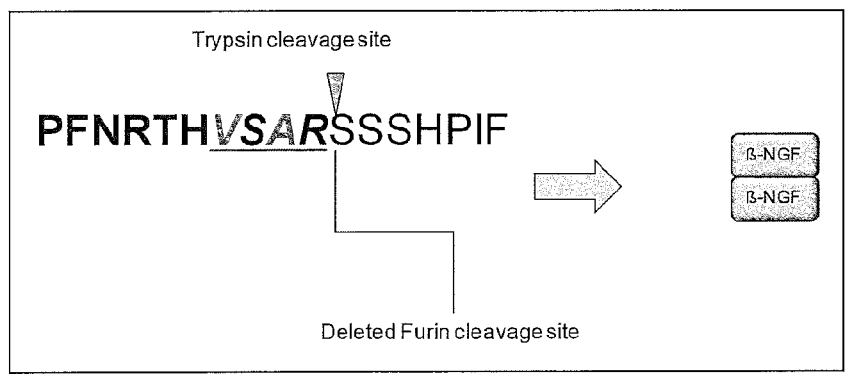

Figure 3. Refolding of proNGF mutant SP174-101
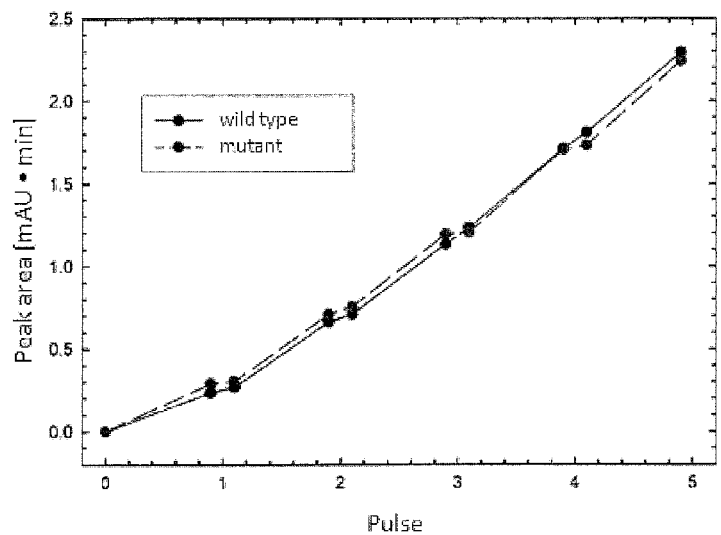
Figure 4. Purification of proNGF SP174-101 by a MEP column
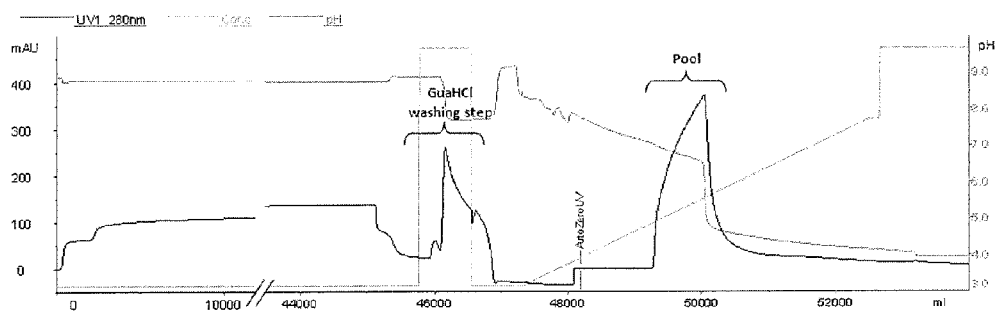

Figure 5. Cleaving proNGF mutant SP174-101 to obtain active beta-NGF
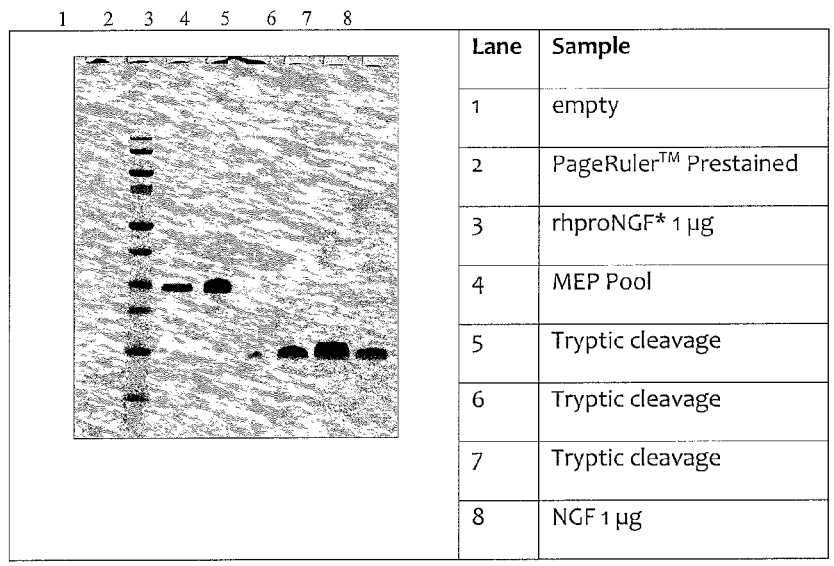
Figure 6. Purification of beta-NGF by SP Sepharose HP chromatography.
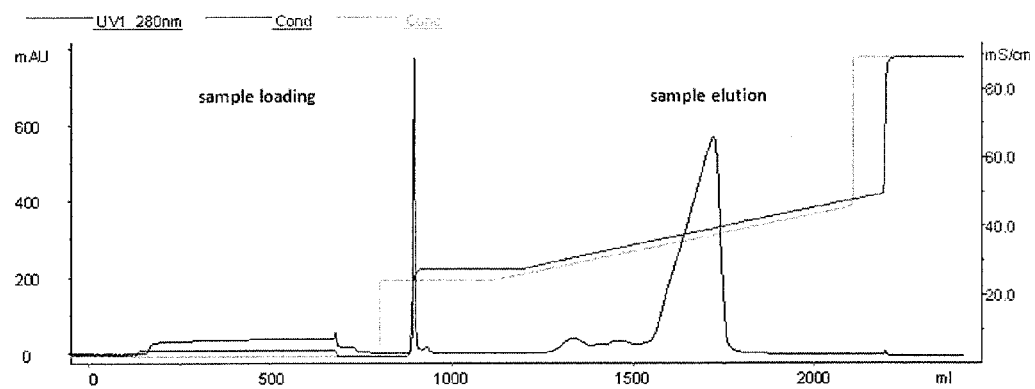

Figure 7. The structure of the proprietary expression vector pSCIL101
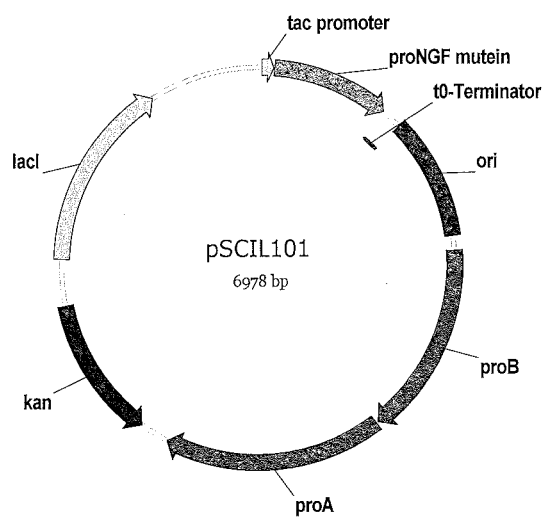

SEQUENCE LISTING

```
<160> NUMBER OF SEQ ID NOS: 15

<210> SEQ ID NO 1
<211> LENGTH: 222
<212> TYPE: PRT
<213> ORGANISM: homo sapiens

<400> SEQUENCE: 1

Met Glu Pro His Ser Glu Ser Asn Val Pro Ala Gly His Thr Ile Pro
1               5                   10                  15

Gln Val His Trp Thr Lys Leu Gln His Ser Leu Asp Thr Ala Leu Arg
            20                  25                  30

Arg Ala Arg Ser Ala Pro Ala Ala Ala Ile Ala Ala Arg Val Ala Gly
        35                  40                  45

Gln Thr Arg Asn Ile Thr Val Asp Pro Arg Leu Phe Lys Lys Arg Arg
    50                  55                  60

Leu Arg Ser Pro Arg Val Leu Phe Ser Thr Gln Pro Pro Arg Glu Ala
65                  70                  75                  80

Ala Asp Thr Gln Asp Leu Asp Phe Glu Val Gly Gly Ala Ala Pro Phe
                85                  90                  95

Asn Arg Thr His Arg Ser Lys Arg Ser Ser Ser His Pro Ile Phe His
```

```
                 100                 105                 110
Arg Gly Glu Phe Ser Val Cys Asp Ser Val Ser Val Trp Val Gly Asp
            115                 120                 125
Lys Thr Thr Ala Thr Asp Ile Lys Gly Lys Glu Val Met Val Leu Gly
            130                 135                 140
Glu Val Asn Ile Asn Asn Ser Val Phe Lys Gln Tyr Phe Phe Glu Thr
145                 150                 155                 160
Lys Cys Arg Asp Pro Asn Pro Val Asp Ser Gly Cys Arg Gly Ile Asp
            165                 170                 175
Ser Lys His Trp Asn Ser Tyr Cys Thr Thr Thr His Thr Phe Val Lys
            180                 185                 190
Ala Leu Thr Met Asp Gly Lys Gln Ala Ala Trp Arg Phe Ile Arg Ile
            195                 200                 205
Asp Thr Ala Cys Val Cys Val Leu Ser Arg Lys Ala Val Arg
            210                 215                 220

<210> SEQ ID NO 2
<211> LENGTH: 222
<212> TYPE: PRT
<213> ORGANISM: artificial
<220> FEATURE:
<223> OTHER INFORMATION: Sequence of a proNGF mutant
<220> FEATURE:
<221> NAME/KEY: misc_feature
<222> LOCATION: (103)..(103)
<223> OTHER INFORMATION: Xaa is a non-basic amino acid or Histidine

<400> SEQUENCE: 2

Met Glu Pro His Ser Glu Ser Asn Val Pro Ala Gly His Thr Ile Pro
1               5                   10                  15
Gln Val His Trp Thr Lys Leu Gln His Ser Leu Asp Thr Ala Leu Arg
            20                  25                  30
Arg Ala Arg Ser Ala Pro Ala Ala Ala Ile Ala Ala Arg Val Ala Gly
            35                  40                  45
Gln Thr Arg Asn Ile Thr Val Asp Pro Arg Leu Phe Lys Lys Arg Arg
        50                  55                  60
Leu Arg Ser Pro Arg Val Leu Phe Ser Thr Gln Pro Pro Arg Glu Ala
65                  70                  75                  80
Ala Asp Thr Gln Asp Leu Asp Phe Glu Val Gly Gly Ala Ala Pro Phe
                85                  90                  95
Asn Arg Thr His Val Ser Xaa Arg Ser Ser Ser His Pro Ile Phe His
            100                 105                 110
Arg Gly Glu Phe Ser Val Cys Asp Ser Val Ser Val Trp Val Gly Asp
            115                 120                 125
Lys Thr Thr Ala Thr Asp Ile Lys Gly Lys Glu Val Met Val Leu Gly
            130                 135                 140
Glu Val Asn Ile Asn Asn Ser Val Phe Lys Gln Tyr Phe Phe Glu Thr
145                 150                 155                 160
Lys Cys Arg Asp Pro Asn Pro Val Asp Ser Gly Cys Arg Gly Ile Asp
            165                 170                 175
Ser Lys His Trp Asn Ser Tyr Cys Thr Thr Thr His Thr Phe Val Lys
            180                 185                 190
Ala Leu Thr Met Asp Gly Lys Gln Ala Ala Trp Arg Phe Ile Arg Ile
            195                 200                 205
Asp Thr Ala Cys Val Cys Val Leu Ser Arg Lys Ala Val Arg
            210                 215                 220
```

```
<210> SEQ ID NO 3
<211> LENGTH: 222
<212> TYPE: PRT
<213> ORGANISM: artificial
<220> FEATURE:
<223> OTHER INFORMATION: proNGF mutant
<220> FEATURE:
<221> NAME/KEY: misc_feature
<222> LOCATION: (101)..(101)
<223> OTHER INFORMATION: Xaa is a non-basic amino acid or Histidine
<220> FEATURE:
<221> NAME/KEY: misc_feature
<222> LOCATION: (103)..(103)
<223> OTHER INFORMATION: Xaa is a non-basic amino acid or Histidine

<400> SEQUENCE: 3

Met Glu Pro His Ser Glu Ser Asn Val Pro Ala Gly His Thr Ile Pro
1               5                   10                  15

Gln Val His Trp Thr Lys Leu Gln His Ser Leu Asp Thr Ala Leu Arg
            20                  25                  30

Arg Ala Arg Ser Ala Pro Ala Ala Ile Ala Ala Arg Val Ala Gly
        35                  40                  45

Gln Thr Arg Asn Ile Thr Val Asp Pro Arg Leu Phe Lys Lys Arg Arg
    50                  55                  60

Leu Arg Ser Pro Arg Val Leu Phe Ser Thr Gln Pro Pro Arg Glu Ala
65                  70                  75                  80

Ala Asp Thr Gln Asp Leu Asp Phe Glu Val Gly Gly Ala Ala Pro Phe
                85                  90                  95

Asn Arg Thr His Xaa Ser Xaa Arg Ser Ser His Pro Ile Phe His
            100                 105                 110

Arg Gly Glu Phe Ser Val Cys Asp Ser Val Ser Val Trp Val Gly Asp
        115                 120                 125

Lys Thr Thr Ala Thr Asp Ile Lys Gly Lys Glu Val Met Val Leu Gly
130                 135                 140

Glu Val Asn Ile Asn Asn Ser Val Phe Lys Gln Tyr Phe Phe Glu Thr
145                 150                 155                 160

Lys Cys Arg Asp Pro Asn Pro Val Asp Ser Gly Cys Arg Gly Ile Asp
                165                 170                 175

Ser Lys His Trp Asn Ser Tyr Cys Thr Thr Thr His Thr Phe Val Lys
            180                 185                 190

Ala Leu Thr Met Asp Gly Lys Gln Ala Ala Trp Arg Phe Ile Arg Ile
        195                 200                 205

Asp Thr Ala Cys Val Cys Val Leu Ser Arg Lys Ala Val Arg
    210                 215                 220

<210> SEQ ID NO 4
<211> LENGTH: 222
<212> TYPE: PRT
<213> ORGANISM: artificial
<220> FEATURE:
<223> OTHER INFORMATION: proNGF mutant
<220> FEATURE:
<221> NAME/KEY: misc_feature
<222> LOCATION: (101)..(101)
<223> OTHER INFORMATION: Xaa is a non-basic amino acid or Histidine

<400> SEQUENCE: 4

Met Glu Pro His Ser Glu Ser Asn Val Pro Ala Gly His Thr Ile Pro
1               5                   10                  15

Gln Val His Trp Thr Lys Leu Gln His Ser Leu Asp Thr Ala Leu Arg
            20                  25                  30
```

```
Arg Ala Arg Ser Ala Pro Ala Ala Ile Ala Ala Arg Val Ala Gly
            35                  40                  45

Gln Thr Arg Asn Ile Thr Val Asp Pro Arg Leu Phe Lys Lys Arg Arg
 50                  55                  60

Leu Arg Ser Pro Arg Val Leu Phe Ser Thr Gln Pro Pro Arg Glu Ala
 65                  70                  75                  80

Ala Asp Thr Gln Asp Leu Asp Phe Glu Val Gly Gly Ala Ala Pro Phe
                 85                  90                  95

Asn Arg Thr His Xaa Ser Ala Arg Ser Ser His Pro Ile Phe His
            100                 105                 110

Arg Gly Glu Phe Ser Val Cys Asp Ser Val Ser Val Trp Val Gly Asp
            115                 120                 125

Lys Thr Thr Ala Thr Asp Ile Lys Gly Lys Glu Val Met Val Leu Gly
130                 135                 140

Glu Val Asn Ile Asn Asn Ser Val Phe Lys Gln Tyr Phe Phe Glu Thr
145                 150                 155                 160

Lys Cys Arg Asp Pro Asn Pro Val Asp Ser Gly Cys Arg Gly Ile Asp
                165                 170                 175

Ser Lys His Trp Asn Ser Tyr Cys Thr Thr Thr His Thr Phe Val Lys
            180                 185                 190

Ala Leu Thr Met Asp Gly Lys Gln Ala Ala Trp Arg Phe Ile Arg Ile
            195                 200                 205

Asp Thr Ala Cys Val Cys Val Leu Ser Arg Lys Ala Val Arg
            210                 215                 220

<210> SEQ ID NO 5
<211> LENGTH: 222
<212> TYPE: PRT
<213> ORGANISM: artificial
<220> FEATURE:
<223> OTHER INFORMATION: proNGF mutant SP174-101

<400> SEQUENCE: 5

Met Glu Pro His Ser Glu Ser Asn Val Pro Ala Gly His Thr Ile Pro
 1               5                  10                  15

Gln Val His Trp Thr Lys Leu Gln His Ser Leu Asp Thr Ala Leu Arg
                 20                  25                  30

Arg Ala Arg Ser Ala Pro Ala Ala Ile Ala Ala Arg Val Ala Gly
            35                  40                  45

Gln Thr Arg Asn Ile Thr Val Asp Pro Arg Leu Phe Lys Lys Arg Arg
 50                  55                  60

Leu Arg Ser Pro Arg Val Leu Phe Ser Thr Gln Pro Pro Arg Glu Ala
 65                  70                  75                  80

Ala Asp Thr Gln Asp Leu Asp Phe Glu Val Gly Gly Ala Ala Pro Phe
                 85                  90                  95

Asn Arg Thr His Val Ser Ala Arg Ser Ser His Pro Ile Phe His
            100                 105                 110

Arg Gly Glu Phe Ser Val Cys Asp Ser Val Ser Val Trp Val Gly Asp
            115                 120                 125

Lys Thr Thr Ala Thr Asp Ile Lys Gly Lys Glu Val Met Val Leu Gly
130                 135                 140

Glu Val Asn Ile Asn Asn Ser Val Phe Lys Gln Tyr Phe Phe Glu Thr
145                 150                 155                 160

Lys Cys Arg Asp Pro Asn Pro Val Asp Ser Gly Cys Arg Gly Ile Asp
                165                 170                 175
```

```
Ser Lys His Trp Asn Ser Tyr Cys Thr Thr Thr His Thr Phe Val Lys
        180                 185                 190

Ala Leu Thr Met Asp Gly Lys Gln Ala Ala Trp Arg Phe Ile Arg Ile
        195                 200                 205

Asp Thr Ala Cys Val Cys Val Leu Ser Arg Lys Ala Val Arg
        210                 215                 220

<210> SEQ ID NO 6
<211> LENGTH: 4
<212> TYPE: PRT
<213> ORGANISM: artificial
<220> FEATURE:
<223> OTHER INFORMATION: protease cleavage site
<220> FEATURE:
<221> NAME/KEY: misc_feature
<222> LOCATION: (2)..(2)
<223> OTHER INFORMATION: Xaa is a non-basic amino acid or Histidine

<400> SEQUENCE: 6

Arg Xaa Lys Arg
1

<210> SEQ ID NO 7
<211> LENGTH: 222
<212> TYPE: PRT
<213> ORGANISM: artificial
<220> FEATURE:
<223> OTHER INFORMATION: Sequence of a proNGF mutant
<220> FEATURE:
<221> NAME/KEY: misc_feature
<222> LOCATION: (101)..(103)
<223> OTHER INFORMATION: Xaa is a non-basic amino acid or Histidine

<400> SEQUENCE: 7

Met Glu Pro His Ser Glu Ser Asn Val Pro Ala Gly His Thr Ile Pro
1               5                   10                  15

Gln Val His Trp Thr Lys Leu Gln His Ser Leu Asp Thr Ala Leu Arg
            20                  25                  30

Arg Ala Arg Ser Ala Pro Ala Ala Ile Ala Ala Arg Val Ala Gly
        35                  40                  45

Gln Thr Arg Asn Ile Thr Val Asp Pro Arg Leu Phe Lys Lys Arg Arg
    50                  55                  60

Leu Arg Ser Pro Arg Val Leu Phe Ser Thr Gln Pro Pro Arg Glu Ala
65                  70                  75                  80

Ala Asp Thr Gln Asp Leu Asp Phe Glu Val Gly Gly Ala Ala Pro Phe
                85                  90                  95

Asn Arg Thr His Xaa Xaa Xaa Arg Ser Ser Ser His Pro Ile Phe His
            100                 105                 110

Arg Gly Glu Phe Ser Val Cys Asp Ser Val Ser Val Trp Val Gly Asp
        115                 120                 125

Lys Thr Thr Ala Thr Asp Ile Lys Gly Lys Glu Val Met Val Leu Gly
    130                 135                 140

Glu Val Asn Ile Asn Asn Ser Val Phe Lys Gln Tyr Phe Phe Glu Thr
145                 150                 155                 160

Lys Cys Arg Asp Pro Asn Pro Val Asp Ser Gly Cys Arg Gly Ile Asp
                165                 170                 175

Ser Lys His Trp Asn Ser Tyr Cys Thr Thr Thr His Thr Phe Val Lys
            180                 185                 190

Ala Leu Thr Met Asp Gly Lys Gln Ala Ala Trp Arg Phe Ile Arg Ile
        195                 200                 205
```

```
Asp Thr Ala Cys Val Cys Val Leu Ser Arg Lys Ala Val Arg
    210                 215                 220

<210> SEQ ID NO 8
<211> LENGTH: 222
<212> TYPE: PRT
<213> ORGANISM: artificial
<220> FEATURE:
<223> OTHER INFORMATION: Sequence of a proNGF mutant
<220> FEATURE:
<221> NAME/KEY: misc_feature
<222> LOCATION: (102)..(102)
<223> OTHER INFORMATION: Xaa is a non-basic amino acid or Histidine

<400> SEQUENCE: 8

Met Glu Pro His Ser Glu Ser Asn Val Pro Ala Gly His Thr Ile Pro
1               5                   10                  15

Gln Val His Trp Thr Lys Leu Gln His Ser Leu Asp Thr Ala Leu Arg
            20                  25                  30

Arg Ala Arg Ser Ala Pro Ala Ala Ala Ile Ala Ala Arg Val Ala Gly
        35                  40                  45

Gln Thr Arg Asn Ile Thr Val Asp Pro Arg Leu Phe Lys Lys Arg Arg
    50                  55                  60

Leu Arg Ser Pro Arg Val Leu Phe Ser Thr Gln Pro Pro Arg Glu Ala
65                  70                  75                  80

Ala Asp Thr Gln Asp Leu Asp Phe Glu Val Gly Gly Ala Ala Pro Phe
                85                  90                  95

Asn Arg Thr His Val Xaa Ala Arg Ser Ser Ser His Pro Ile Phe His
            100                 105                 110

Arg Gly Glu Phe Ser Val Cys Asp Ser Val Ser Val Trp Val Gly Asp
        115                 120                 125

Lys Thr Thr Ala Thr Asp Ile Lys Gly Lys Glu Val Met Val Leu Gly
    130                 135                 140

Glu Val Asn Ile Asn Asn Ser Val Phe Lys Gln Tyr Phe Phe Glu Thr
145                 150                 155                 160

Lys Cys Arg Asp Pro Asn Pro Val Asp Ser Gly Cys Arg Gly Ile Asp
                165                 170                 175

Ser Lys His Trp Asn Ser Tyr Cys Thr Thr Thr His Thr Phe Val Lys
            180                 185                 190

Ala Leu Thr Met Asp Gly Lys Gln Ala Ala Trp Arg Phe Ile Arg Ile
        195                 200                 205

Asp Thr Ala Cys Val Cys Val Leu Ser Arg Lys Ala Val Arg
    210                 215                 220

<210> SEQ ID NO 9
<211> LENGTH: 4
<212> TYPE: PRT
<213> ORGANISM: artificial
<220> FEATURE:
<223> OTHER INFORMATION: protease cleavage site

<400> SEQUENCE: 9

Arg Ser Lys Arg
1

<210> SEQ ID NO 10
<211> LENGTH: 4
<212> TYPE: PRT
<213> ORGANISM: artificial
<220> FEATURE:
```

```
<223> OTHER INFORMATION: Protease cleavage site
<220> FEATURE:
<221> NAME/KEY: misc_feature
<222> LOCATION: (3)..(3)
<223> OTHER INFORMATION: Xaa is a non-basic amino acid or Histidine

<400> SEQUENCE: 10

Val Ser Xaa Arg
1

<210> SEQ ID NO 11
<211> LENGTH: 4
<212> TYPE: PRT
<213> ORGANISM: artificial
<220> FEATURE:
<223> OTHER INFORMATION: Protease cleavage site
<220> FEATURE:
<221> NAME/KEY: misc_feature
<222> LOCATION: (1)..(1)
<223> OTHER INFORMATION: Xaa is a non-basic amino acid or Histidine
<220> FEATURE:
<221> NAME/KEY: misc_feature
<222> LOCATION: (3)..(3)
<223> OTHER INFORMATION: Xaa is a non-basic amino acid or Histidine

<400> SEQUENCE: 11

Xaa Ser Xaa Arg
1

<210> SEQ ID NO 12
<211> LENGTH: 4
<212> TYPE: PRT
<213> ORGANISM: artificial
<220> FEATURE:
<223> OTHER INFORMATION: Protease cleavage site
<220> FEATURE:
<221> NAME/KEY: misc_feature
<222> LOCATION: (1)..(1)
<223> OTHER INFORMATION: Xaa is a non-basic amino acid or Histidine

<400> SEQUENCE: 12

Xaa Ser Ala Arg
1

<210> SEQ ID NO 13
<211> LENGTH: 4
<212> TYPE: PRT
<213> ORGANISM: artificial
<220> FEATURE:
<223> OTHER INFORMATION: Protease cleavage site

<400> SEQUENCE: 13

Val Ser Ala Arg
1

<210> SEQ ID NO 14
<211> LENGTH: 4
<212> TYPE: PRT
<213> ORGANISM: artificial
<220> FEATURE:
<223> OTHER INFORMATION: Protease cleavage site
<220> FEATURE:
<221> NAME/KEY: misc_feature
<222> LOCATION: (1)..(3)
<223> OTHER INFORMATION: Xaa is a non-basic amino acid or Histidine

<400> SEQUENCE: 14

Xaa Xaa Xaa Arg
1
```

```
<210> SEQ ID NO 15
<211> LENGTH: 4
<212> TYPE: PRT
<213> ORGANISM: artificial
<220> FEATURE:
<223> OTHER INFORMATION: Protease cleavage site
<220> FEATURE:
<221> NAME/KEY: misc_feature
<222> LOCATION: (2)..(2)
<223> OTHER INFORMATION: Xaa is a non-basic amino acid or Histidine

<400> SEQUENCE: 15

Val Xaa Ala Arg
1
```

PRONGF MUTANTS AND USES THEREOF IN THE PRODUCTION OF BETA-NGF

CROSS-REFERENCE TO RELATED APPLICTIONS

This application is a divisional of U.S. patent application Ser. No. 14/366,460 filed Jun. 18, 2014, and issued as U.S. Pat. No. 9,617,322 on Apr. 11, 2017, which is a 35 U.S.C. 371 National Stage Patent Application of International Application No. PCT/EP2012/076251, filed Dec. 19, 2012, which claims benefit of priority to European application 11194208.2, filed Dec. 19, 2011; the contents all of which are hereby incorporated by reference.

FIELD OF THE INVENTION

The present invention relates to novel proNGF mutants having substitutions at the native protease cleavage site. The present invention further discloses a method of producing a biologically active human beta-NGF from an inactive insoluble proNGF mutant and the use of a proNGF mutant for producing human beta-NGF.

BACKGROUND OF THE INVENTION

Nerve growth factor (beta-NGF) is a neurotrophic factor playing a crucial role in the growth and survival of neurons (sensory and sympathetic) (Levi-Montalcini, R., Science 237 (1987) 1154; Thoenen, H., et al., Physiol. Rev. 60 (1980) 1284; Yankner, B. A., et al., Annu. Rev. Biochem. 51 (1982) 845). Beta-NGF belongs to a cysteine-knot superfamily of growth factors assuming stable dimeric protein structure. Furthermore, beta-NGF promotes the growth, differentiation and vitality of cholinergic neurons of the central nervous system (Hefti, F. J., J. Neurobiol. 25 (1994) 1418). Possible therapeutic indications for recombinant human nerve growth factor include peripheral sensory neuropathies, e.g. associated with diabetes or as a possible side effect in AIDS therapy. Other indications for beta-NGF are central neuropathies, e.g. Alzheimer's disease. In this case, the loss of memory is the result of a loss of cholinergic neurons. Beta-NGF has also been found to be effective in the treatment of human cutaneous and corneal ulcers (Bernabei et al. Lancet 1999; Lambiase et al. NEJM 1998). Moreover, Beta-NGF has also been shown to protect retinal cells from degeneration and apoptosis in an experimental animal model of glaucoma and to improve visual function in a few patients affected by glaucoma (Lambiase A, et al. PNAS 2009).

Mature human beta-NGF is a 118 amino acid protein which is translated as a preproprotein consisting of 241 amino acids. The signal peptide (prepeptide) of 18 amino acids is cleaved during translocation into the endoplasmic reticulum (ER). The resulting proprotein (proNGF) is processed at its N-terminus by removing the pro-sequence by protease cleavage. Mature human NGF shows a high degree of identity (about 90%) to rodent (murine and rat) beta-NGF. For clinical studies or therapeutic uses, beta-NGF has to be provided in high concentrations. Submaxillary glands of mice are a natural source of beta-NGF. However, these beta-NGF preparations are heterogeneous mixtures of different dimers and thus not suitable for therapeutic uses. Furthermore, it is desirable to administer the human form of the protein to patients. In human tissue, however, neurotrophic factors are present only in low concentrations.

The prosequence is a domain separate from the mature protein (see the sequence data in FIG. 1, wherein the prosequence is indicated in bold). These two domains are separated by an exposed protease cleavage site with a basic amino acid target sequence of the type Arg-Ser-Lys-Arg located at positions 101 to 104 of the human proNGF sequence (SEQ ID NO: 1). This motif is naturally a cleavage site for the serine endoprotease Furin. Additionally, the cleavage site may be specifically processed by other suitable proteases, preferably by proteases with substrate specificity of cleavage after the amino acid Arginine (Arg, R). For example, the protease trypsin cleaves after basic amino acids such as Lysine (Lys, K) or Arginine (Arg, R).

Methods for the preparation of biologically active beta-NGF from its inactive proform are well-known in the field of the art. For example, EP 0 994 188 B1 describes a method for the preparation of biologically active beta-NGF from its inactive pro-form having a poor solubility. According to this method, beta-NGF is obtainable from recombinant insoluble inactive proNGF which solubilized in a denaturing solution. Afterwards, the solubilized proNGF is transferred into a non- or weakly denaturing solution. The denatured proNGF assumes a biologically active conformation as determined by the disulfide bonds present in native beta-NGF. Subsequently, the prosequence of proNGF is cleaved off whereby active beta-NGF is obtained.

Human proNGF contains a native protease (Furin) cleavage site Arg-Ser-Lys-Arg, thus having the following sequence motif: $R^1SK^3R^4$. For specific production processes such as those requiring "Good Manufacturing Practice" (GMP) quality levels, materials such as enzymes have to be provided in high quality. The protease Furin is currently not available as GMP-grade protease.

Therefore, an alternative protease, Trypsin (EC 3.4.21.4), was chosen to cleave proNGF to result in a mature beta-NGF protein. The serine protease Trypsin cleaves peptide chains at the carboxyl side of basic amino acids Arginine or Lysine. In human proNGF, the naturally occurring cleavage site in human proNGF contains three positions with basic amino acids (positions 101, 103, and 104 of SEQ ID NO: 1; alternatively referred to as $R^1$, $K^3$ and $R^4$ herein). Thus, cleavage of proNGF by Trypsin may lead to numerous different cleaved products depending on where exactly cleavage occurs. Typical cleavage products are $SK^3R^4$-beta-NGF and $R^4$-beta-NGF and mature beta-NGF. This problem is exacerbated since dimerization of the beta-NGF protein will lead to an even higher number (up to six) of inhomogenous products which have to be purified in following steps (see FIG. 2a).

TECHNICAL PROBLEMS UNDERLYING THE PRESENT INVENTION AND THEIR SOLUTION

Methods for producing betaNGF have been described in the prior art. However, the currently available production processes have several drawbacks, such as inhomogenous beta-NGF products and low yields of beta-NGF.

Cleavage of the wild-type pro-NGF with Trypsin to produce beta-NGF has shown low efficiency that obliges to use very high amounts of the enzyme in order to obtain a sufficient yield of cleaved beta-NGF. This has several drawbacks that impact on the subsequent process of purification. First of all, it further decreases the selectivity of the cleavage which leads to several products of digestion. Secondly, the purification of beta-NGF from the enzyme is necessary since the enzyme has to be absent in the final sample of the protein. This implies several purification procedures to remove the abundant Trypsin. Thus, the use of Trypsin as cleavage enzyme in the procedure of the prior art leads either to very low yields of beta-NGF or to problems of purification of the protein.

Needless to say that there remains a need in the art for a method of producing beta-NGF without the drawbacks as described above. It is thus a problem underlying the present invention to provide a novel method of producing beta-NGF to be obtained in high quality, high efficiency and in high yields. Further, it is a problem underlying the invention to provide a production process for beta-NGF which results in high yields of beta-NGF, is efficient, robust, scalable and reproducible.

An advantage of the invention is the production of a beta-NGF from a novel proNGF mutant. The novel mutant results in homogenous beta-NGF products in good yield because the novel proNGF mutant prevents inhomogeneous digestion by proteases and thus inhomogenous beta-NGF products. The problem of the invention is solved by providing the proNGF mutant of the invention and the method of producing beta-NGF from the proNGF mutant as described by the present invention.

The novel mutant results in an unexpected and striking increase in the efficiency of the cleavage of trypsin at the relevant site in the mutated proNGF of the invention compared to the wild type. This allows to use extremely low amounts of the protease trypsin as compared to the amount to be used on the wild type and, as a consequence, results in reduced problems of purification of beta NGF from the enzyme itself and from by products of the cleavage.

The above-described problems are solved and the advantages are achieved by the subject-matter of the independent claims. Preferred embodiments of the invention are included in the dependent claims as well as in the following description, examples and figures.

The above overview does not necessarily describe all problems solved by the present invention. Further problems and how there are solved may be apparent for the skilled person after having studied the present application.

SUMMARY OF THE INVENTION

In a first aspect the present invention relates to a proNGF mutant, wherein the protease cleavage site $R^1SK^3R^4$ is substituted at least at positions $R^1$ and $K^3$ corresponding to positions 101 and 103 of the human wildtype proNGF sequence (SEQ ID NO: 1) by an amino acid selected from non-basic amino acids and Histidine.

In a second aspect the present invention relates to a method of preparing a biologically active human beta-NGF from an inactive insoluble proNGF mutant substituted at the native protease cleavage site $R^1SK^3R^4$ at least at positions $R^1$ and $K^3$ corresponding to positions 101 and 103 of the human wildtype proNGF sequence (SEQ ID NO: 1), comprising (i) providing a proNGF mutant according to this invention, and (ii) cleaving the proNGF mutant in order to obtain active human beta-NGF.

In particular, the invention relates to the following process:
   a. dissolving the proNGF mutant in a denaturating solution;
   b. transferring the proNGF mutant into a refolding solution where the denatured proNGF assumes a biologically active conformation;
   c. purifying the proNGF mutant from the refolding solution;
   d. cleaving the pro-sequence of the proNGF mutant to obtain the active beta-NGF.

A third aspect of the invention relates to the use of a proNGF mutant wherein at least Arginine at position 101 and the Lysine at position 103 of the native protease cleavage site $R^1SK^3R^4$ at positions 101 to 104 of the human wildtype proNGF (SEQ ID NO: 1) is substituted by non-basic amino acids for the preparation of human beta-NGF.

A further aspect of the present invention relates to pharmaceutical compositions comprising beta-NGF produced from the proNGF mutant wherein at least Arginine at position 101 and Lysine at position 103 of the native protease cleavage site $R^1SK^3R^4$ at positions 101 to 104 of the human wildtype proNGF (SEQ ID NO: 1) are substituted by an amino acid selected from non-basic amino acids and Histidine and a pharmaceutically acceptable carrier or diluent.

This summary of the invention does not necessarily describe all features of the present invention. Other embodiments will become apparent from a review of the ensuing detailed description.

DETAILED DESCRIPTION OF THE INVENTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents (for example: patents, patent applications, scientific publications, instructions etc.) are cited throughout the text of this specification. Nothing herein is to be construed as an admission that the invention is not entitled to antedate such disclosure by virtue of prior invention.

Sequences: All sequences referred to herein are disclosed in the attached sequence listing that, with its whole content and disclosure, is a part of this specification.

The term "about" when used in connection with a numerical value is meant to encompass numerical values within a range having a lower limit that is 5% smaller than the indicated numerical value and having an upper limit that is 5% larger than the indicated numerical value.

The term "proNGF" or "pro-NGF" refers to the pro-form of human beta-NGF. The full human proNGF sequence is defined in SEQ ID NO: 1 (FIG. 1a). In order to obtain mature beta-NGF, the propeptide proNGF has to be cleaved by proteases. The prosequence of beta-NGF is a domain separate from the mature beta-NGF. Between these two domains, there is a native protease cleavage site Arg-Ser-Lys-Arg (referred herein to $R^1SK^3R^4$, SEQ ID NO: 9) at positions 101 to 104 of SEQ ID NO: 1. The cleavage site may be specifically processed by suitable proteases, in particular furin protease.

The term "proNGF mutant" or "proNGF mutein" refers to modifications of the pro-form of human beta-NGF by substitutions of amino acids. The proNGF mutein of the present invention is substituted at the native protease cleavage site $R^1SK^3R^4$ (SEQ ID NO: 9) at least at both positions $K^3$ and $R^1$ corresponding to positions 101 and 103 of the human wild type proNGF sequence (SEQ ID NO: 1) by an amino acid selected from non-basic amino acids and Histidine.

In a preferred embodiment of the invention, amino acid Lysine in Position $K^3$ (corresponding to position 103) is substituted with Alanine (see FIG. 1d, SEQ ID NO: 4, FIG. 1e, SEQ ID NO: 5, FIG. 1g, SEQ ID NO: 8).

In another preferred embodiment of the invention, amino acid Arginine in position $R^1$ (corresponding to position 101) is substituted with Valine (see FIG. 1b, SEQ ID NO: 2, FIG. 1e, SEQ ID NO: 5, FIG. 1g, SEQ ID NO: 8).

In another embodiment of the invention, the amino acid arginine $R^4$ corresponding to position 104 of the wildtype proNGF sequence (SEQ ID NO: 1) may also be substituted by any amino acid which allows processing of the proNGF by proteolytic cleavage to obtain beta NGF, preferably a basic amino acid such as Arginine or Lysine. For example, the presence of Alanine in Position $R^4$ avoids processing of proNGF to beta NGF. Therefore, the mutant of invention cannot contain Alanine in position 104.

TABLE 1

Protease cleavage sites of pro NGF and proNGF muteins

| SEQ ID NO: | Protease cleavage site (pos. 101-104 of SEQ ID NO: 1) |
|---|---|
| 1 | RSKR (wild-type) |
| 2 | VSXR |
| 3 | XSXR |
| 4 | XSAR |
| 5 | VSAR |
| 6 | XXXR |
| 7 | VXAR |

(X refers to any amino acid but not Arg or Lys)

The term "non-basic amino acid" refers to any amino acid which is not positively charged. The term refers to an amino acid residue other than a basic amino acid. The term excludes amino acids Lysine or Arginine which are amino acids with positive side chains. Non-basic amino acids are negatively charged amino acids Glutamic Acid and Aspartic Acid, amino acids with polar uncharged side chains (Serine, Threonine, Asparagine, Glutamine), amino acids with hydrophobic side chains (Alanine, Valine, Isoleucine, Leucine, Methionine, Phenylalanine, Tyrosine, Tryptophane) and amino acids Cysteine, Glycine and Proline.

The term "biologically active pro-NGF" or "proNGF with biologically active conformation" as such refers to the biological activity of pro-NGF. A biologically active conformation of proNGF is determined by the presence of disulfide bridges occurring in natural beta-NGF. The activity may be, for example, determined according to an assay as described by Chevalier et al. 1994, Blood 83: 1479-1485, 1994, which is incorporated herein by reference. Example 11 describes an assay for the biological activity of proNGF via stimulation of the proliferation of TF1 cells.

The twin "beta-NGF" refers to a mature beta-nerve growth factor, preferably from human. The sequence for the mature beta-nerve growth factor is shown in FIG. 1 (SEQ ID NO: 1, SEQ ID NO: 2, SEQ ID NO: 3, SEQ ID NO: 4 and SEQ ID NO: 5, SEQ ID NO: 7, and SEQ ID NO: 8), starting at position 105.

The term "activity of beta-NGF" or "biologically active beta-NGF" as such means the biological activity of beta-NGF. Biologically active beta-NGF exists in the form of a dimer. Beta-NGF must be present in a dimeric form to have a biologically active conformation. The prerequisite of a biologically active conformation of beta-NGF is the correct formation of the disulfide bridges to a cystine knot. The activity may be, for example, determined according to the DRG assay (dorsal root ganglion assay), see for example Levi-Montalcini, R. et al., Cancer Res. 14 (1954) 49, and Varon, S. et al., Meth. in Neurochemistry 3 (1972) 203. In this assay the stimulation and survival of sensory neurons from dissociated dorsal root ganglia of chick embryos is monitored by means of neurite formation.

The term "substitution" or "substitutions" refers to modifications of the pro-form of human beta-NGF by replacement of amino acids. The term comprises the chemical modification of amino acids by e.g. substituting or adding chemical groups or residues to the original amino acid. The step of modification of the selected amino acids is performed preferably by mutagenesis on the genetic level. Preferably, the modification of proNGF is carried out by means of methods of genetic engineering for the alteration of a DNA belonging to proNGF.

The modifications are mutations that cause the replacement of a single base nucleotide with another nucleotide of the genetic material. Point mutations results in encoding different amino acids compared to the wild-type sequence. Preferably, expression of the modified proNGF protein is then carried out in prokaryotic or eukaryotic organisms, most preferably in prokaryotic organisms.

The term "denaturating" or "denaturation" refers to a process in which the folding structure of a protein is altered. The term refers to unfold the tertiary structure of proNGF or proNGF mutein. The alteration of the folding structure is due to exposure to certain chemical or physical factors. As a result, some of the original properties of the protein, especially its biological activity, are diminished or eliminated. Due to the denaturing process, proteins become biologically inactive. Further, denatured proteins can exhibit a wide range of characteristics, including loss of biological function, loss of solubility and/or aggregation.

The term "refolding" or "renaturating" or "renaturation" refers to a process by which the protein structure assumes its native functional fold or conformation. Due to renaturation or refolding processes, the protein becomes biologically active.

The term "recombinant" refers to the cloning of DNA into vectors for the expression of the protein encoded by the DNA in a suitable host. The host is preferably a prokaryote, most preferably a bacterium. A "recombinant expression" as used herein refers to expression of proNGF or the proNGF mutein in in prokaryotic host cells, for example E. coli strains suitable for expression of recombinant proteins could be used.

The term "soluble" refers to a protein which is susceptible of being dissolved in some solvent.

The term "insoluble" refers to a protein which is not susceptible of being dissolved in some solvent.

DESCRIPTION OF THE INVENTION

ProNGF Mutants of the Invention

In a first embodiment of the invention, the present invention provides a proNGF mutant wherein the protease cleavage site $R^1SK^3R^4$ is substituted at least at positions $R^1$ and $K^3$ corresponding to positions 101 and 103 of the human wildtype proNGF sequence (SEQ ID NO: 1) by an amino acid selected from non-basic amino acids and Histidine. In other words, at least Arginine $R^1$ at position 101 and the Lysine $K^3$ at position 103 of the native protease cleavage site $R^1SK^3R^4$ at positions 101 to 104 of the human wild type proNGF sequence (SEQ ID NO: 1) are substituted by any amino acid but not Arginine or Lysine.

In the human wildtype proNGF (SEQ ID NO: 1), the native protease cleavage side refers to amino acids positions 101 to 104 (ArgSerLysArg, RSKR, SEQ ID NO: 9). Amino acid Lysine $K^3$ in position 103 of the wild-type proNGF sequence and amino acid Arginine $R^1$ in position 101 are replaced with any amino acid but not Arg or Lys to result in a proNGF with improved properties in particular for producing beta-NGF. In order to achieve the above-identified object, i.e. to generate a mutein with improved features for producing beta-NGF, Arginine (R') or Lysine ($K^3$) may be substituted by all naturally occurring amino acids, or artificial amino acids as well, provided they do not constitute a cleavage site for trypsin.

According to the invention, the amino acid modifications to one or more positions corresponding to residues 101-103 may be substitutions that replace basic amino acids with non-basic amino acids. Theses substitutions can be used to create proNGF mutants according to the invention, in particular, for the production of beta-NGF. Mutants comprise substitutions at least at positions Arg101 and Lys103. The amino acid residues are replaced by a non-basic amino acid or Histidine. Particularly, the mutants of the invention have the substitutions Arg101Val and Lys103Ala. For example, said natural non-basic amino acids may be selected from the group consisting of the naturally occurring amino acid residues Alanine, Asparagine, Aspartic Acid, Cysteine, Glutamine, Glutamic Acid, Glycine, Isoleucine, Leucine, Methionine, Phenylalanine, Proline, Serine, Threonine, Tryptophan, Tyrosine, Valine.

Amino acids for substitutions at positions 101 and 103 are not selected from basic (positively charged) amino acids Arginine (Arg) and Lysine (Lys). Also less preferred are amino acids Isoleucine (Ile), Leucine (Leu), or Phenylalanine (Phe), Cysteine (Cys), Proline (Pro) or Tryptophan (Trp). Serine (Ser) is naturally occurring in position 102 of the human proNGF wild-type sequence. X in position 102 (SEQ ID NO: 7 and SEQ ID NO: 8) is preferably selected from Serine (Ser) which is naturally occurring in position 102 of the human proNGF sequence, but may also be selected from any other amino acid wherein the amino acid must be a non-basic amino acid (i.e. not Arginine or Lysine). It is important that the amino acid in position 102 is a non-basic amino acid (i.e. not Arg or Lys).

The amino acid in position 104 of the wild-type human proNGF sequence is preferably Arginine (Arg) which is naturally occurring in position 104 of the human proNGF sequence, but may also be substituted by any other amino acid, preferably a basic amino acid, more preferably Lysine, which allows processing of the proNGF by proteolytic cleavage to obtain beta NGF.

For example, the presence of Alanine in position 104 of wild-type human proNGF avoids processing of proNGF to beta NGF. Thus, Ala in position 104 is excluded.

Table 2 summarizes the preferred substitutions for the protease cleavage site of proNGF.

TABLE 2

Preferred amino acids in positions 101-104 of wild-type proNGF
The star (*) shows the naturally occurring amino acid in the protease cleavage site (wild-type proNGF, SEQ ID NO: 1).

| | |
|---|---|
| 101 | Val, Ala, Asn, Asp, Glu, Gln, Gly, Ser, Thr, Tyr, Met, His, Cys, Pro, Phe, Trp, Ile, Leu |
| 102 | Ser*, Gly, Asp, Tyr, Thr, Asn, Glu, Ala, Val, Gln, His, Met, Cys, Pro, Phe, Trp, Ile, Leu |
| 103 | Ala, Val, Asp, Asn, Glu, Gln, Gly, Ser, Thr, Tyr, Met, His, Cys, Pro, Phe, Trp, Ile, Leu |
| 104 | Arg*, Lys |

Amino acids Cys, Pro, Phe, Trp, Ile and Leu are less preferred substitutions at Positions 101, 102, and 103.

Most preferred amino acids in positions 101-104 of wild-type proNGF

| | |
|---|---|
| 101 | Val, Ala, Gly, Ser, Thr, Asn, Asp, Glu, Gln, Tyr, Met, His |
| 102 | Ser*, Val, Ala, Gly, Thr, Asn, Asp, Glu, Gln, Tyr, Met, His |
| 103 | Ala, Val, Gly, Ser, Thr, Asn, Asp, Glu, Gln, Tyr, Met, His |
| 104 | Arg*, Lys |

It is essential that there are any amino acid but not Arg or Lys at positions 101, 102, and 103 of the proNGF-mutein and that there is a basic amino acid (Arg or Lys) at position 104 of the proNGF-mutein. It was surprisingly shown that specifically two amino acid replacements in positions 101 and 103 result in high efficiencies of beta-NGF production.

In the sequence of the most preferred proNGF mutant of the invention (SEQ ID NO: 5), the preferred substituted amino acid in position 101 of human wild-type proNGF is Valine, in position 103 of human wild-type proNGF is Alanine, in position 102 of human wild-type proNGF Serine, and in position 104 of human wild-type proNGF Arginine. In particularly preferred embodiment of the invention, the proNGF mutant of the invention presents has a sequence corresponding to that of SEQ ID NO: 5.

The present invention is also directed to nucleic acids coding for the proNGF mutants described herein as well.

Method of Preparing a Human Beta-NGF from a proNGF Mutant of the Invention

In a second aspect, the present invention is directed to a method of preparing a biologically active human beta-NGF from an inactive insoluble proNGF mutant substituted at the native protease cleavage site $R^1SK^3R^4$ (SEQ ID NO: 9) at positions 101 and 103 ($R^1$ and $K^3$) of the human wildtype proNGF sequence (SEQ ID NO: 1), comprising providing a proNGF mutant substituted at the native protease cleavage site $R^1SK^3R^4$ at positions 101 and 103 ($R^1$ and $K^3$) of the human wildtype proNGF sequence, and cleaving the proNGF mutant in order to obtain active human beta-NGF.

Preferably, the proNGF mutant is obtained by recombinant expression in prokaryotic cells. Suitable bacterial strains are well known in the art, e.g., *E. coli, Bacillus* sp., and *Salmonella*, and kits for such expression systems are commercially available. The preferred host cells for recombinant expression are *E. coli*, for example *E. coli* BL21, JM 108/109 (K12), JM106, JM83 and TB1 or derivatives thereof. Any other *E. coli* strain suitable for expression of recombinant proteins could be used.

Polynucleotides are operatively linked to expression control sequences allowing expression of the fusion proteins of the invention in prokaryotic host cells. Such expression control sequences include but are not limited to inducible and non-inducible promoters, operators, repressors and other elements that are known to those skilled in the art and that drive or otherwise regulate gene expression. Such regulatory elements include as for example T7, TAC, PBAD, LAC promoters, Lad, LacI$^Q$ repressors.

The sequence of the proNGF mutant is introduced into the prokaryotic host cell by a suitable vector. Suitable Vectors could be for example but not limited to: pBR322, pMAL, pUC19 and all derivatives. The prokaryotic host cell includes but is not limited to prokaryotic cells such as bacteria (for example, *E. coli* or *B. subtilis*), which can be transformed with, for example, plasmid DNA, recombinant bacteriophage DNA, or cosmid DNA expression vectors containing the polynucleotide molecules of the invention. In one embodiment of the invention, plasmid vectors are use. For example, but by no way limited to, plasmid vectors described in EP1697523B1 may be used (which is incorporated by reference herein).

In order to express proNGF muteins, an expression vector is used that contains
  a. a strong promoter to direct transcription (e.g. a tac or T7 promoter),
  b. a coding sequence for proNGF or proNGF mutein
  c. a transcription/translation terminator (e.g. t0-terminator of the bacteriophage lambda)
  d. a first selectable marker gene, e.g. a gene coding for antibiotic resistance (e.g. Kanamycin resistence, kan),
  e. a second selectable marker gene, e.g. a gene coding for proB and/or proA.
  f. a repressor gene (e.g. a lad gene)
  g. a high copy number origin of replication In one embodiment of the invention, proprietary expression vectors (Scil Proteins GmbH, see EP1697523B1 for the structure of a suitable expression vector) or commercially available vectors may be used for cloning. Regarding general information on the vectors which might be used in the method of the present invention, it is referred to the above mentioned details. However, any suitable vectors might be used as known in the art.

The structure of the proprietary expression vector pSCIL101 as one example for a suitable vector for the transformation of prokaryotic host cells is depicted in FIG. 7.

The method of the preparation of a proNGF mutant is comprising the following initial steps:
  i. preparing a nucleic acid encoding a proNGF mutein
  ii. introducing said nucleic acid into a procaryotic expression vector;
  iii. introducing said expression vector into a host cell;
  iv. cultivating the host cell;
  v. subjecting the host cell to suitable culturing conditions.

Due to its expression in prokaryotic host cells, the proNGF mutein is in the form of its inactive, insoluble form.

In a preferred embodiment, the method of production of beta-NGF from a proNGF mutant according to the present invention comprises the steps of:
  a. dissolving the proNGF mutant substituted at the native protease cleavage site $R^1SK^3R^4$ at positions $R^1$ and $K^3$ corresponding to positions 101 and 103 of the human wildtype proNGF sequence (SEQ ID NO: 1) by solubilisation of inclusion bodies in a denaturating solution;
  b. transferring the proNGF mutant into a refolding solution where the denatured proNGF assumes a biologically active conformation;
  c. purifying the proNGF mutant from the refolding solution;
  d. cleaving the pro-sequence of the proNGF mutant to obtain the active beta-NGF.

In the following, the preferred steps of a method for producing beta-NGF from a proNGF mutant according to the present invention are discussed.

Step a: Solubilisation of proNGF Mutant

Step a) corresponds to dissolving the proNGF mutant substituted at the native protease cleavage site $R^1SK^3R^4$ at positions $R^1$ and $K^3$ corresponding to positions 101 and 103 of the human wildtype proNGF sequence (SEQ ID NO: 1) by solubilisation of inclusion bodies in a denaturating solution. It is noted that the proNGF mutant of the invention in step a) usually is in the form of its inactive, insoluble form due to its expression in prokaryotic host cells. Inactive proNGF showing a poor solubility is formed during overexpression of the protein in the cytosol of prokaryotes. In this case, proNGF prepared by recombination remains in the cytoplasm in an insoluble and aggregated form. These protein aggregates, the isolation thereof as well as their purification are described for example in Marston, F. A., Biochem. J. 240 (1986).

To isolate these inactive protein aggregates (inclusion bodies), the prokaryotic cells are disrupted following fermentation. Cell disruption may be performed by conventional methods, e.g. by means of high pressure homogenization, sonification or lysozyme (Rudolph, R., et al. (1997); Folding proteins. In: Creighton, T. E. (ed.): Protein Function: A Practical Approach. Oxford University Press, pp. 57-99).

Further, the inclusion bodies are solubilized. Inclusion bodies (TB) are accumulations of usually defective or incompletely folded proteins. They form inside cells, for example bacteria cells, such as *E. coli*, in the event of excessive expression of recombinant proteins. The inclusion bodies employed according to the invention preferably comprise the proNGF mutein. This means that they contain at least 60, at least 70, at least 80 or at least 90 wt. % of pro-NGF (based on the total amount of protein).

The invention provides a method for the production of proNGF mutein thereof, wherein inclusion bodies which non-folded, inactive, insoluble proNGF mutein or a derivative thereof are solubilized in a denaturing buffer (solution).

The denaturating solution of step a) preferably comprises a solution containing (i) a chaotropic agent, (ii) a chelator, (iii) a buffer, and (iv) a reducing agent.

The denaturation buffer comprises at least one chaotropic substance (agent). Chemical substances which dissolve ordered hydrogen bridge bonds in water are called chaotropic. Since the hydrogen bridge bonds are broken open, the chaotropic substances interfere with the water structure and ensure disorder (increase in entropy). The reason for this is that the formation of the $H_2O$ cage structures necessary for the solvation is prevented. In the case of amino acids, they reduce the hydrophobic effects and have a denaturing action on proteins, since a driving force of protein folding is the assembling together of hydrophobic amino acids in water. Generally, any substance which exerts the hydrophobic effect in the solubilization buffer and therefore has a denaturing action on the proteins can be employed as a chaotropic substance. Chaotropic substances are in general salts or low molecular weight compounds, such as urea. Chaotropic substances are clearly distinguished from detergents, since they contain no hydrophobic radical, such as an alkyl radical, in the molecule. Generally, the chaotropic action is accompanied by an improvement in the solubility of the protein, in this case the prethrombin.

In a preferred embodiment of the invention, the chaotropic compound is chosen from guanidinium salts, in particular guanidinium hydrochloride and guanidinium thiocyanate, iodides, barium salts, thiocyanates, urea and perchlorates.

The chaotropic compounds are employed in conventional amounts. For example, 4-8 M guanidinium hydrochloride or 4-9 M urea can be employed.

The denaturation buffer comprises a reducing agent compound, for example a disulphide compound such as Glutathione (GSH). The disulphide compound is capable of forming mixed disulphides with thiol groups (—SH) of cysteines of the polypeptides in the inclusion bodies. The disulphide is added to the solution. The disulphide does not designate proteins which the inclusion bodies comprise and which possibly comprise disulphide bridges. Preferably, the disulphide is not a true peptide. Preferably, the disulphide is a low molecular weight compound. The molecular weight is, for example, lower than 2,000 g/mol or than 1,000 g/mol. The disulphide is employed, for example, in a concentration of from 5 mM to 1 M, in particular 10 mM to 0.5 M.

In a preferred embodiment of the invention, the disulphide compound is glutathione disulphide. Glutathione (GSH), also γ-L-glutamyl-L-cysteinylglycine, is a pseudotripeptide which is formed from the three amino acids glutamic acid, cysteine and glycine. GSH is present in the cytoplasm of both prokaryotes and eukaryotes and is involved in the formation of disulphide bridges. It is in equilibrium with the dimer GSSG, which contains a disulphide bridge. Glutathione reacts with cysteines R—SH and R'—SH from two polypeptides or from a single polypeptide in a disulphide exchange reaction:

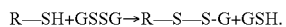

RSSG is called a mixed disulphide. It is reacted with a further cysteine of a polypeptide, so that as a result a disulphide bridge is obtained between two cysteines:

Glutathione is kept enzymatically in the reduced form (GSH) in the cytosol. "Reducing conditions" in the cytosol are therefore referred to. Conditions are established in the solubilization buffer so that the disulphide compound it comprises catalyses the formation of disulphide bridges in accordance with the reactions described above. The GSSG is employed, for example, in a concentration of from 10 mM to 0.5 M.

Alternatively, as reducing agent (reductant), Cysteine might be used.

In a preferred embodiment of the invention, the denaturation solution is a Tris buffer.

The denaturation solution can comprise further conventional additives, for example EDTA or salts. The pH of the solubilization buffer is, for example, between 7 and 10, preferably pH 8. The solubilization is preferably assisted mechanically, for example with conventional homogenization apparatuses or by means of ultrasound. After the solubilization, solids which remain are preferably separated off. The supernatant comprises the solubilized pro-NGF.

In one embodiment of the invention, the denaturing solution comprises i. Guanidinium-HCl, 1-8 M, preferably 4-6 M, most preferred 4 M, GSH or Cysteine, 1-100 mM, preferably 5 mM
ii. Tris, 0.01-1 M, preferably 0.1 M,
iii. EDTA, 1-50 mM, preferably 10 mM
iv. pH 7.0-10.0, preferably pH 8.0

A concentration of 4 M Guanidinium-HCl is in most cases sufficient for a complete denaturation of proNGF mutein.

Step b: Refolding of the proNGF Mutant

After the solubilization of the proNGF mutant from inclusion bodies it is, necessary to refold the protein in its native conformation. For the refolding process it is important to minimize the competing reactions misfolding and aggregation. To prevent aggregation the refolding is performed at very low protein concentrations because aggregation of the protein is predominant at high protein concentrations. In step b), transferring the proNGF mutant into a refolding buffer occurs where the denatured proNGF assumes a biologically active conformation. A biologically active conformation can be determined by the presence of disulfide bridges occurring in natural beta-NGF.

In a preferred embodiment of the invention, the solubilized proNGF mutant is renatured in a refolding solution which contains at least one chaperone, at least one a metal chelator, and a redox shuffling system.

In a preferred embodiment, the method according to the present invention uses a refolding solution in step b) comprising
  i. a chaperone, preferably Arginine, 0.5-1.0 M, preferably 0.75 M,
  ii. a metal chelator, preferably EDTA, 1-10 mM, preferably 5 mM,
  iii. a redox shuffling system, at 0.1-10 mM, preferably 1 mM L-Cystine and 5 mM L-Cysteine, or 1 mM GSSG (oxidized glutathione) and 5 mM GSH (reduced glutathi-one).
  iv. pH 8.0-pH 11.0, preferably pH 9.5

Alternative redox shuffling systems such as Cystamin/Cysteamin could be used.

In a preferred embodiment of the invention, the folding assistant is Arginine. Compounds which promote the folding of proteins can generally be employed as "folding assistants". Such compounds are known to the person skilled in the art. They can assist the folding in various ways. It is assumed that arginine destabilizes incorrectly folded intermediates, so that these are at least partly unfolded again (from a thermodynamic dead-end) and therefore can be correctly folded again. On the other hand, glycerol usually stabilises proteins. Compounds which increase the absolute yield of folded pro-NGF mutein in the method according to the invention by more than 5%, in particular by more than 10% or more than 20% (based on the total amount of pro-NGF employed for the folding), compared with a method without using the folding assistant, are suitable in particular as folding assistants.

The refolding is preferably carried out at a pH of between 8 and 11, in particular pH 9.5.

To increase the protein concentration in the refolding vessel, a pulse renaturation was carried out. Limiting for the number of pulses is the Guanidinium-HCl concentration which should not exceed 0.3 M. The protein concentration per pulse should not exceed 50 μg/ml in relation to the final refolding volume.

In a preferred embodiment of the invention, the solubilisate is added to the folding batch in several fractions or continuously over several days. Preferably, the solubilisate is added in a "pulse renaturing" by rapid dilution to the solubilisate. In this context, for example but by no means limited to, at least 6 pulses could be performed in a time interval of, for example, 24 hours. The number of pulses is set such that after the addition of the solubilization batch the concentration of protein which has not yet been folded is not too high, since otherwise aggregates are obtained. For example, with each pulse 0.05 g/l to 0.2 g/l, preferably 0.1 g/l of protein is newly transferred into the folding batch (based on the protein concentration in the folding batch after addition of the solubilisate). For example, each refolding step takes at least 1-2 h.

After refolding, the refolding reaction needs to be clarified before loading onto a column. This can be done by any methods known in the art, for example, by filtration.

In a preferred embodiment, the method for producing a correctly folded pro-NGF mutant includes the following steps: a) Inclusion bodies which comprise insoluble proNGF mutant are solubilized in a denaturing solution as described above, and b) the solubilized pro-NGF is then renatured in a refolding solution buffer as described above.

In a preferred embodiment of the invention, the denaturing solution and/or the refolding solution consequently contains no detergent. It has been found, that the use of detergents is not necessary for the solubilization and/or folding of pro-NGF mutein. This is advantageous, since certain detergents are comparatively aggressive chemical substances which pharmaceutical products should not comprise or should comprise in only small amounts and therefore must be removed in an expensive manner. The method according to the invention is therefore advantageous compared with the method of Soejima et al., 2001, in which such aggressive detergents (Triton X-100 or Brij-58) are employed for folding the protein. In other words, no detergents are used in the entire production method according to the invention, and the production method is therefore detergent-free.

Step c: Purification of proNGF Mutant by Chromatography

By carrying out the method according to the invention with the denaturation and subsequent refolding, an aqueous solution of folded pro-NGF mutein is obtained. The folded pro-NGF mutein can subsequently be purified further by known methods.

In a preferred embodiment the proNGF mutant is purified from the refolding (e.g. non- or weak denaturing) solution via chromatographic purification, in particular by means of a mixed mode chromatography (step c of the method of production of beta NGF from a proNGF mutant of the invention). The most preferred column for the chromatography is a column with a synthetic affinity ligand, preferably 4-mercapto-ethyl-pyridine (MEP Hypercell; Pall). Advantages of this medium are that the binding is independent of the ionic strength, salt stacking is not necessary and higher flow rates to fasten the process are possible. Further, the elution is done by a pH-shift.

Other mixed mode material columns are known and could be used. For example, but not limited to, MEP (Pall; affinity ligand is 4-Mercapto ethyl pyridine), HEA (Pall; affinity ligand: Hexylamino), PPA (Pall, affinity ligand: Phenylpropylamino), MBI (Pall; affinity ligand: 2-Mercapto-5benzamidazole sulfo acid), Capto MMC (GEHC), Capto adhere (GEHC; affinity ligand: N-benzyl-N-methyl ethanolamine), CHT hydroxyapatite (BioRad), CHT fluoroapatite). The MEP, HEA, PPA, and MBI columns have a hydrophobic binding, where Capto MMC is a cation exchanger with mixed mode functionality and Capto adhere is an anion exchanger with mixed mode functionality. The BioRad columns are ion exchange columns with hydrophobic components. Any other mixed mode material column not listed here could also be used to purify the proNGF mutant.

Step d: Cleavage of proNGF to Beta-NGF proNGF is the precursor of beta-NGF. Thus, in step d) of the method of production of beta-NGF from a proNGF mutant of the invention, the pro-sequence of the proNGF mutant is cleaved in order to obtain an active beta-NGF.

Proteases having trypsin-like substrate specificity cleave the protein without digesting the active portion of the protein molecule. Trypsin-like proteases cleave peptide bonds following a positively charged amino acid such as Arginine or Lysine. As trypsin-like proteases, several serine proteases (serine endopeptidases) are considered for processing of the proNGF to result beta-NGF. Preferably, the serine protease Trypsin is used for the cleavage of the pro-sequence but other proteases could be used instead.

It is noted that cleavage is not restricted to trypsin itself, but may involve other proteases having trypsin-like substrates as well. Generally, if the ratio of proNGF to trypsin (or other protease) is appropriately adjusted, the correctly folded, mature beta-NGF will not be cleaved by this protease. In contrast, denatured proteins as well as folding intermediates expose sequences which are susceptible to an attack by the protease.

Preferably for the cleavage of proNGF mutant to beta-NGF, the ratio of trypsin (or other protease) to proNGF mutant is from 1:200-1:100.000, more preferably from 1:5.000-1:20.000 per weight, most preferred is a ratio of 1:10.000 (w/w). In a most preferred embodiment, the cleavage occurs for 8-23 hours at room temperature, most preferred 18 hours. Under the conditions used in this invention, proNGF mutant is cleaved completely and almost no by-products are formed. No aggregation was observed.

As clearly described in the Examples, the present inventors have found that the amino acid modifications introduced in the proNGF mutant of the invention not only avoid cleavage of the protein at undesired cleavage sites but also unexpectedly result in a great increase in the efficiency of the cleavage of Trypsin compared to that of the wild type proNGF, which allows to carry out the cleavage under very selective conditions to obtain a very pure product.

In details, the experimental data clearly show that at already a very low Trypsin/Protein ratio such as 1:100.000, the proNGF mutant of the invention (SEQ ID NO: 5) results in very high purity recombinant human beta-NGF with a high cleavage yield (about 85%). Furthermore, wild type proNGF (SEQ ID NO: 1) at the same Trypsin/Protein ratio shows a low cleavage yield (about 5%). A satisfactory yield is only obtained at much higher trypsin/protein ratios (1/250), but this is accompanied by low selectivity and a high product degradation due to overdigestion.

Step e: Further Purification of Beta-NGF

The beta-NGF produced from a proNGF mutant of the invention is further purified, for example, by several chromatographic methods. Further purification steps are required to separate Trypsin and product related impurities of the tryptic digestion from beta-NGF. Purification steps should reduce HCPs, Endotoxins, and DNA. Any methods known in the art for protein purification can be used. Most preferred are chromatographic purifications, for example with Sepharose columns (e.g. SP Sepharose HP, Q Sepharose FF).

The final product beta-NGF produced from a proNGF was analyzed regarding its purity by SDS-PAGE, rp-HPLC, SE-HPLC, and IEX-HPLC. HPLC analyses revealed a purity of beta-NGF of at least 97%.

In a preferred embodiment of the invention, the method for the production of a pro-NGF mutein suitable for obtaining beta-NGF includes the following steps:
a) expression of a recombinant pro-NGF mutant with substituted protease cleavage site in prokaryotic cells
b) isolation of the pro-NGF mutein-containing inclusion bodies,
c) mixing of the inclusion bodies with a suitable denaturing buffer comprising at least (i) a chaotropic substance, (ii) a chelator, (iii) a buffer, and (iv) a reducing agent
d) refolding in a refolding solution comprising at least a chaperone, a metal chelator, and a redox shuffling system,
e) purification of the refolded pro-NGF mutant,
f) cleavage into the active form of beta-NGF with proteases such as trypsin
g) isolation and purification of the beta-NGF.

Use of proNGF for the Production of Beta-NGF

In a third aspect, the invention is directed to the use of the proNGF mutant of the present invention for producing human beta-NGF.

Pharmaceutical Composition of betaNGF Obtained from proNGF Mutants of the Invention In a further aspect, the invention is directed to a pharmaceutical composition comprising betaNGF obtained from a proNGF-mutant being substituted at the native protease cleavage site $R^1SK^3R^4$ at positions 101 and 103 ($K^3$ and $R^1$) of the human wildtype proNGF sequence (SEQ ID NO: 1) as described above and a pharmaceutically acceptable carrier.

In one embodiment of the invention, the pharmaceutically active beta-NGF is administered to the patient by gene-therapeutical methods. In gene therapy, there are two basic methods available, suitable for introducing a gene, in the present case a gene coding for a beta-NGF, into the patient.

In the ex vivo application, the pharmaceutically active gene encoding beta-NGF is introduced in a body cell by a vector, where the body cell preferably is a glial cell, and the cell treated in this way then is re-introduced into the patient, for example by micro- or nanoparticles. Particularly preferred is a specific integration of the beta-NGF gene in the cellular genome.

In the in vivo-gene therapy, the beta-NGF gene is transported to target cells in the body by vectors, for example by means of viruses, which on the one hand may infect the target cell und, thus, will be able to introduce the pharmaceutically active beta-NGF gene, but, on the other hand, are not able to reproduce themselves within the target cell. In this approach, nano- or microparticles, for example liposomes, which may fuse with the cell membrane, may be used a vectors as well.

As a vector for the beta-NGF gene, a virus or an antibody might be used as an example, capable of specifically infecting the host cell or which immunoreacts with an antigen in the target cell. As a viral vehicle, retroviruses might be used as an example. Furthermore, it is possible to use adenoviruses or Vaccinia based vectors, for example, modified vaccinia virus Ankara (MVA).

The skilled person will be able to select a suitable formulation based on routine considerations and will chose a suitable form for administering the present pharmaceutical composition to a patient. For example, the pharmaceutical composition might comprise one or more pharmaceutically acceptable ingredients, for example carriers or diluents. Among these classes of substances, one might name fillers, salts, buffers, stabilisators, penetration enhancers and other well-known materials. Techniques for the formulation of pharmaceutical compositions of the present invention may be found in well-known standard textbooks such as "Remington's Pharmaceutical Sciences", Mack Publishing Co., Easton, Pa., latest edition.

The dosage of the betaNGF obtained by the method of production as described in the present invention might be in a range of 0.1 µg/kg to 500 µg/kg body weight, if administered by infusion, and from 2 µg/kg to 2 mg/kg body weight if administered by injection.

BRIEF DESCRIPTION OF THE DRAWINGS

FIG. 1 shows the sequence of pro-NGF and of the pro-NGF mutants of the invention.

Shown in bold letters is the sequence of the proform of human beta-NGF. Shown in bold and underlined is the protease (trypsin) cleavage site (amino acids 101-104 of SEQ ID NO: 1; trypsin cleavage sites are between amino acids 101-102 ($R^1$), 103-104 ($K^3$) and 104-105 ($R^4$)). X in the sequence can be any amino acid.

FIG. 1a shows a sequence of human proNGF (SEQ ID NO: 1) with protease cleavage site RSKR (SEQ ID NO: 9).

FIG. 1b shows a sequence of a proNGF mutant of the invention (SEQ ID NO: 2) with the protease cleavage site VSXR (SEQ ID NO: 10).

FIG. 1c shows a sequence of a proNGF mutant of the invention (SEQ ID NO: 3) with the protease cleavage site mutated to XSXR (SEQ ID NO: 11).

FIG. 1d shows a sequence of a proNGF mutant of the invention (SEQ ID NO: 4) with the protease cleavage site mutated to XSAR (SEQ ID NO: 12).

FIG. 1e shows a sequence of a proNGF mutant of the invention (SEQ ID NO: 5) with the protease cleavage site mutated to VSAR (SEQ ID NO: 13).

FIG. 1f shows a sequence of a proNGF mutant of the invention (SEQ ID NO: 7) with the protease cleavage site mutated to XXXR (SEQ ID NO: 14).

FIG. 1g shows a sequence of a proNGF mutant of the invention (SEQ ID NO: 8) with the protease cleavage site mutated to VXAR (SEQ ID NO: 15).

FIG. 1h shows sequences of protease cleaving sites (SEQ ID NO:s 6, 9-15).

FIG. 2. Processing of proNGF or pro NGF mutants to beta-NGF

FIG. 2a shows six beta NGF cleavage products after trypsin cleavage by using the wild type proNGF having a native furin cleavage site RSKR. The drawing clearly shows that a cleavage of wild type proNGF to betaNGF results in an inhomogenous mixture of many different cleavage products.

FIG. 2b shows native beta NGF cleavage products after trypsin cleavage by using a proNGF mutant SP174-101 (SEQ ID NO: 5) with deletion of the native furin cleavage site. The protease cleavage site RSKR (SEQ ID NO: 9) was substituted by two amino acids to result a site VSAR (SEQ ID NO: 12). This site can only be cleaved by a protease after the amino acid Arginine in position 104; Trypsin can only cleave at one cleavage site (instead of three). The drawing clearly shows that a cleavage of mutant proNGF SP174-101 (SEQ ID NO: 5) to beta-NGF results in only one homogenous cleavage product (beta-NGF).

FIG. 3 shows the refolding of the proNGF mutant SP174-101 (SEQ ID NO: 5) compared to wild type proNGF. The figure compares the refolding yield of the wild type proNGF (continuous line) and the proNGF mutant (broken line) with the protease cleavage site mutated to VSAR. It can be clearly seen from the figure that the refolding efficiency of wild type and mutant proNGF is identical.

FIG. 4 shows the purification of a proNGF mutant SP174-101 with the protease cleavage site mutated to VSAR (SEQ ID NO: 5) by a MEP HyperCel column. The figure shows an elution profile of MEP HyperCel purification of a refolded and filtrated proNGF mutant.

FIG. 5 shows the cleavage of a proNGF mutant SP174-101 with the protease cleavage site mutated to VSAR (SEQ ID NO: 5) by Trypsin. The figure shows a Coomassie stained SDS-PAGE gel of fractions of the tryptic cleavage. The tryptic cleavage product of the proNGF mutant can be seen in lanes 4-7. The figures clearly show that the purified proNGF mutant results in only one cleavage product (beta-NGF).

FIG. 6 shows the purification of beta-NGF. The figure shows a profile of a SP Sepharose HP column after the tryptic cleavage. The tryptic digestion reaction was loaded onto a SP Sepharose HP column. The elution was done in three steps (a. 25% 25 mM sodium phosphate, 1 M NaCl, pH 6.5 (buffer B), b. in a linear gradient from 25-50% buffer B, and c. 100% buffer B (flow rate 60 cm/h)).

FIG. 7 shows the structure of the proprietary expression vector pSCIL101.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used but some experimental errors and deviations should be accounted for. Unless indicated otherwise, molecular weight is average molecular weight, temperature is in degrees Centigrade, and pressure is at or near atmospheric.

Example 1

Substitution of Wild-type Pro NGF at the Protease Cleavage Site at Positions 101 to 104 ($R^1SK^3R^4$)

Substitution of Arginine $R^1$ and Lysine $K^3$ corresponding to positions 101 and 103 of human pro-NGF (SEQ ID NO: 1) was realized on DNA level using a synthesized gene by methods as known to someone skilled in the art. Serine in position 102 either remained unchanged or substitution of position 102 of human pro-NGF (SEQ ID NO: 1) was also realized on DNA level using a synthesized gene by methods as known to someone skilled in the art. Lysine $K^4$ corresponding to position 104 was not substituted. Sequences are shown in FIG. 1.

Example 2

Recombinant Expression of proNGF Mutant SP174-101 (SEQ ID NO: 5) in Prokaryotic Cells The bacterial host *E. coli* JM108 used for expression of rh-proNGF (DSMZ 5585; thi Δ (lac-proAB) endAI gyrA96 relA1 phx hsdR17 supE44 recA) is proline-auxotrophic, which was neutralized by the use of the plasmid with the designation pSCIL101. The plasmid pSCIL101 is based on the plasmid pSCIL008 (see WO05061716). The strain cannot synthezise thiamine (Vieira & Messing, 1982 *Gene*. October; 19(3):259-68). The pro-NGF mutant shown in SEQ ID NO: 5 is expressed under the control of the tac promoter located on pSCIL101. The vector pSCIL101 used here is a high copy plasmid with a kanamycin resistance. The expression is carried out in defined mineral salt medium and is induced by the addition of IPTG. The pro-NGF mutant is deposited in the cytosol in the form of inclusion bodies (IBs).

Cell Line:
  host strain, e.g. *E. coli* HMS174 (K12) or JM108 (K12)
  proNGF mutant SP174-101 (SEQ ID NO: 5)
  Tac promoter (IPTG induction)
  ColE1 replicon
  Kanamycin resistance
  proBA selection
  Proprietary vector system pSCIL 101 (e.g. see WO05/061716)

Example 3

Fermentation

The aim of this fermentation was to obtain product and biomass for subsequent process steps. To monitor the overexpression of the target protein during the fermentation process, samples were analyzed by means of SDS-PAGE before and after induction.

Mineral salt medium without antibiotics
Batch phase $\mu \approx 0.25$ $h^{-1}$ ($OD_{end}=18$)
Fed batch phase I exponential feeding with $\mu_{set}=0.18$ $h^{-1}$
Fed batch phase II: constant feed rate
Point of induction $OD_{end}=60\pm5$
1.0 mM IPTG
Time of induction 5 h
Final OD=82±4
Process time 28.5 h±1.25
Plasmid Stability 100%
Yield: 40 mg/g proNGF; 1.2 g/L±0.2 g/L proNGF Example 4

Primary Recovery of Inclusion Bodies Containing SP174-101

In bacterial cells, the recombinant protein is present in the form of aggregates. The expression of the pro-NGF mutein took place in the form of IBs. The cell breakdown and the IB preparation were carried out in accordance with standard protocols and can be conducted on the laboratory scale up to a working up of approx. 200 g of biomass. The preparation of these "inclusion bodies" containing the proNGF mutein was performed according to Rudolph, R., et al. (1987); Folding proteins. In: Creighton, T. E. (ed.): Protein Function: A Practical Approach. Oxford University Press, pp. 57-99, and according to EP0994188B1. For cell disruption, the cell pellets were resuspended in a suitable buffer and subsequently the cells were disrupted using high pressure homogenization in 50 mM Natriumphosphat pH 7.0, 1 mM EDTA.

Example 5

Dissolving the proNGF Mutant SP174-101 in a Denaturating Solution (Solubilization of Inclusion Bodies)

The inclusion bodies were solubilized in a denaturing solution which comprised a solution (i) a chaotropic agent, (ii) a chelator, (iii) a buffer, and (iv) a reducing agent. For solubilization, Guanidinium HCl (GuaHCl) was tested in a concentration range of 4.0-6.0 M. The solubilization buffer was mixed in different ratios with a inclusion-body slurry (IB slurry). All experiments had a final Cysteine concentration of 5 mM and were carried out at room temperature. Results were analyzed by SDS-PAGE (data not shown). The experiments revealed that a concentration of 4 M GuaHCL was sufficient for complete solubilization of inclusion bodies. The ratio of inclusion body-slurry to buffer is 1+1.25 (v/v) (IB slurry:buffer). The final conditions of the denaturing solution for solubilization of inclusion bodies were:

i. 4 M Guanidinium-HCl,
ii. 0.1 M Tris,
iii. 10 mM EDTA iv. 5 mM Cysteine
v. pH 8.0

The solubilisate is clarified by depth filtration according to standard procedures.

The protein concentration was then determined using the method of Bradford (Bradford, M. M., Anal. Biochem. 72 (1976) 248). The protein concentration of proNGF mutein was between 10-20 mg/ml.

Example 6

Transferring the proNGF Mutant SP174-101 into a Refolding Buffer where the Denatured proNGF Assumes a Biologically Active Conformation After solubilization, it is necessary to refold the protein in its native conformation and thereby minimize misfolding and aggregation. To prepare biologically active proNGF mutein according to the invention from solubilized materials, these were diluted into a refolding solution wherein proNGF assumes a biologically active conformation.

The final refolding solution for the solubilizate based on IB-slurry comprised
i. 0.75 M Arginine
ii. 5 mM EDTA
iii. 1 mM L-Cystine and 5 mM L-Cysteine
iv. pH 9.5

The obtainment of NGF in the active conformation was confirmed by the presence of the disulfide bridges occurring in mature human beta-NGF.

To increase protein concentration in the refolding process, a pulse renaturation was carried out. A pulse was given every hour per 50 μg/ml proNGF mutant protein. The concentration of Guanidinium-HCl in the solution should not exceed 0.3 M. In order to achieve this, 15 pulses were required. The clarified refolded fraction was filtered before loading to further columns.

The performance of the refolding reaction was analysed after every pulse by rp-HPLC. The resulting peak area was blotted against the number of pulses. For the rp-HPLC, a reversed-phase column (e.g., 214MS54, 4.6×250 mm; 300 Å, 5 Vydac) with guard column (e.g. 214GK54; 300 Å; Vydac) was used. The running buffers were $H_2O$ with 0.05% trifluoroacetic acid (TFA) and Acetonitrile with 0.05% TFA. The flow rate was 1 mL/min. Results are shown in FIG. 3. It can be seen from FIG. 3 that the refolding efficiency of wild type and mutant proNGF is identical.

Example 7

Purifying the proNGF Mutant SP174-101 from the Refolding Solution Via a Mixed Mode Material Column A column with a synthetic affinity ligand, 4-mercapto-ethyl-pyridine (MEP) was used. The elution was done by shifting the pH-value. Further, elution was carried out with a low salt concentration which is beneficial for an efficient process design.

The column was equilibrated with 0.75 M Arginine, 5 mM EDTA, pH 9.5. The clarified refolding reaction was loaded onto MEP HyperCel column (Pall) with a maximal loading capacity of 5 g proNGF mutant per L column media. In the washing step, most impurities and unbound protein were depleted by using buffer 2 M GuaHCl, 0.1 M Tris-HCl, pH 8.0 and 10 mM Tris-HCl, pH 8.0. The elution was done in a linear gradient from 0-70% 50 mM Acetate, pH 4.0 (flow rate 120 cm/h). FIG. 4 shows an elution profile of MEP HyperCel purification of a refolded and filtrated proNGF mutant with the protease cleavage site mutated to VSAR (SEQ ID NO: 5) of the invention. At the GuaHCL washing step "many impurities were removed. At "pool", about 60-70% of the proNGF mutant was recovered.

Example 8

Cleaving the proNGF Mutant SP174-101 to Obtain Active Beta-NGF

For the tryptic digestion of proNGF mutant to beta-NGF, such a Phosphatebuffer was used, which do not inhibit the activity of the protease. Sodium phosphate buffer was added to the MEP-eluate to a final concentration of 25 mM sodium phosphate. The pH-value was adjusted to pH 6.5. For proteolysis, Trypsin (Roche, GMP grade) was added in a ratio of 1:10,000 (w/w) (trypsin:proNGF). The proteolysis was carried out using an incubation time of 18 h at room temperature. Performance and yield of the tryptic digestion were analyzed by SDS-PAGE, rp-HPLC and UV/VIS280 nm. FIG. 5 shows an SDS-PAGE of fractions of the tryptic cleavage. A 4-12% Bis/Tris-Gel, 1 mm, 1×MES as running buffer (Invitrogen) was used. Lanes 5-7 show the tryptic cleavage products compared to the uncleaved proNGF mutant (rhproNGF*, see lane 3) and to the mature beta-NGF (NGF; see lane 8). The figures clearly show that the purified proNGF mutant results in only one cleavage product (beta-NGF). A complete digestion of proNGF mutant to beta-NGF could be observed.

Example 9

Purification of Active Beta NGF

After the tryptic digestion, beta-NGF was loaded onto a SP Sepharose HP column to deplete Trypsin, by-products of the cleavage and further impurities. The SP Sepharose HP purification is shown in FIG. 6.

The column was equilibrated with 25 mM Na-phosphate buffer (pH 6.5). The tryptic digestion reaction was loaded onto a SP Sepharose HP column (2 g beta-NGF/L medium) and unbound protein washed with the equilibration buffer. The elution was done in three steps (3 cv 25% 25 mM Na-phosphate pH 6.5/1 M NaCl (buffer B), 10 cv in a linear gradient from 25-50% buffer B, and 3 cv 100% buffer B (flow rate 60 cm/h)).

FIG. 6 shows the purification of beta-NGF. The figure shows a profile of a SP Sepharose HP column after the tryptic cleavage. The yield of beta-NGF was 85-95% (peak "sample elution").

Example 10

Cleavage Efficiency of Trypsin on Mutant SP174-101 and Wild Type proNGF

This procedure was applied in parallel for both proNGF-mutant SP174-101 (SEQ ID NO: 5) and human wild-type proNGF (SEQ ID NO: 1; rhProNGF).

5 mL of purified rhProNGF were dialyzed against 25 mM phosphate buffer pH 6.5. Following dialysis, a protein concentration of 0.08 mg/mL was measured by HPLC-UV. Per digestion sample, 80 μg of proNGF were employed. After proteolysis, all samples were analyzed by HPLC-UV.

Mass ratio 1/10.000 w/w of trypsin/rhProNGF mutant was used, while different mass ratios of trypsin/rhProNGF wild type were used (see Table 3). As per trypsin solution 1.0 μg/mL and 10 μg/mL were used. After an overnight incubation (about 17 hours) at room temperature, all samples were analysed. For control porpoises rhProNGF mutant without added protease was also incubated.

TABLE 3

| Trypsin/rhProNGF ratio | Trypsin Volume (μL) | Trypsin Amount (μg) | rhProNGF Type | rhProNGF Volume (μL) | rhProNGF Amount (μg) |
|---|---|---|---|---|---|
| Control | — | | Mutant | 1000 | 80 |
| 1/10000 | 8 (1 μg/mL) | 0.008 | Mutant | 1000 | 80 |
| 1/10000 | 8 (1 μg/mL) | 0.008 | Wild Type | 1000 | 80 |
| 1/5000 | 16 (1 μg/mL) | 0.016 | Wild Type | 1000 | 80 |
| 1/1000 | 8 (10 μg/mL) | 0.08 | Wild Type | 1000 | 80 |
| 1/250 | 32 (10 μg/mL) | 0.32 | Wild Type | 1000 | 80 |

Performances and yields of all tryptic digestions were analysed by HPLC-UV using a Vydac 214MS C4 column.

Table 4 shows the cleavage yields obtained after tryptic digestion. The experimental data clearly show that cleavage of the proNGF mutant SEQ ID NO: 5 with Trypsin results in only one product (beta-NGF) at high cleavage yield (about 85%) using a very low trypsin/protein ratio (1/10.000). This can be compared to the cleavage of the wildtype proNGF (SEQ ID NO: 1) which shows a low cleavage yield (only about 5%) at low trypsin/protein ratio (1/10.000) and a high product degradation (overdigested) at high trypsin/protein ratio (1/250).

TABLE 4

| | Amount μg | Trypsin/ProNGF ratio | % ProNGF | % betaNGF | % betaNGF Over-digested Forms |
|---|---|---|---|---|---|
| ProNGF Standard | 80 | — | 100 | | |
| NGF Standard | 42 | | | 100.0 | |
| ProNGF SEQ ID NO: 5 | 80 | 1/10000 | 1.9 | 84.5 | |
| ProNGF Wild Type | 80 | 1/10000 | 67.1 | 4.6 | — |
| ProNGF Wild Type | 80 | 1/5000 | 21.5 | 18.6 | 6.6 |
| ProNGF Wild Type | 80 | 1/1000 | 0.0 | 77.9 | 12.9 |
| ProNGF Wild Type | 80 | 1/250 | 0.0 | 67.9 | 25.7 |

Example 11

Test for the Biological Activity of proNGF Via Stimulation of the Proliferation of TF1 Cells TF1 cells (ATCC, catalog nr. CRL2003) were cultivated according to standard procedures. A test medium (90% medium RPMI 1640, 10% foetal bovine serume FBS, 50 U/ml Penicillin und 50 μg/ml Streptomycin) was added to the cells and centrifuged. The pellet was resuspended at a density of $1.5 \cdot 10^5$ cells/ml in test medium at 37° C. The cell suspension was mixed with different concentrations of proNGF protein ($10^{-10}$ M, $3 \cdot 10^{-10}$ M, $10^{-9}$ M, $3 \cdot 10^{-9}$ M, $10^{-8}$ M, $3 \cdot 10^{-8}$ M, $10^{-7}$ M, $3 \cdot 10^{-7}$ M, $10^{-6}$ M, $3 \cdot 10^{-6}$ M, $10^{-5}$ M und $3 \cdot 10^{-5}$ M) and analyzed in 96-well-plates. After incubation for 48 h at 37° C., cell proliferation reagent (e.g. WST-1, Roche Applied Science, cat no. 1644807) was added and the plates again incubated for 4 h at 37° C. The absorption was measured at 450 nm and the $EC_{50}$-value determined by using suitable programs (z. Bsp. Sigma-Plot 2000).

The invention claimed is:

1. A method of preparing a biologically active human beta-NGF comprising:
   providing a proNGF mutant wherein the protease cleavage site $R^1SK^3R^4$ is substituted at least at positions R1 and K3 corresponding to positions 101 and 103 of the human wild type proNGF sequence (SEQ ID NO: 1) by any amino acid selected from the group consisting of a non-basic amino acid and Histidine and wherein the amino acid at position $R^4$ corresponding to position 104 of human wild type proNGF sequence (SEQ ID NO: 1) is selected from the group consisting of Arginine or Lysine; and
   cleaving the pros-sequence of the proNGF mutant by a serine protease in order to obtain active human beta-NGF, wherein the ratio of serine protease to pro NGF mutant is 1:5,000-1:20,000 (w/w), 1:10,000 (w/w), or 1:100,000 (w/w).

2. The method of claim 1 further comprising the steps of:

a. dissolving the proNGF mutant by solubilisation of inclusion bodies in a denaturating solution;

b. transferring the proNGF mutant into a refolding solution where the denatured proNGF assumes a biologically active conformation; and c. purifying the refolded proNGF mutant.

3. The method of claim 2, wherein the denaturing solution comprises a solution containing (i) a chaotropic substance, (ii) a chelator, (iii) a buffer, and (iv) a reducing agent.

4. The method of claim 3, wherein the denaturing solution comprises:

i. 1-8 M Guanidinium-HCl, ii. 0.01-1 M Tris, iii. 1-50 mM EDTA, iv. 1-100 mM selected from Gluthione (GSH) or Cysteine, v. pH 7.0-10.0.

5. The method of claim 4, wherein the denaturing solution comprises:

i. 4-6 M Guanidinium-HCl, ii. 0.01-1 M Tris, iii. 1-50 mM EDTA, iv. 1-100 mM selected from Gluthione (GSH) or Cysteine, v. pH 7.0-10.0.

6. The method of claim 5, wherein the denaturing solution comprises:

i. 4 M Guanidinium-HCl, ii. 0.1 M Tris, iii. 10 mM EDTA iv. 5 mM GSH or Cysteine v. pH 8.0.

7. The method according to claim 2 wherein the refolding is carried out as a pulse renaturation.

8. The method of claim 2, wherein the refolding solution comprises:

i. 0.5-1.0 M of a chaperone, ii. 1-10 mM of a metal chelator, iii. 0.1-10 mM of a redox shuffling system, iv. pH 8.0-pH 11.0.

9. The method of claim 8, wherein the refolding solution comprises;

i. 0.75 M Arginine, ii. 5 mM EDTA iii. 1 mM L-Cystine and 5 mM L-Cysteine, or 1 mM GSSG (oxidized glutathione) and 5 mM GSH (reduced glutathione), iv. pH 9.5.

10. The method according to claim 2, wherein the proNGF mutant is purified via mixed mode chromatography.

11. The method according to claim 10, wherein the proNGF mutant is purified using a mixed mode material chromatography column with a synthetic affinity ligand.

12. The method according to claim 11, wherein the chromatography column is a column with a synthetic affinity ligand chosen from the group consisting of 4-mercapto-ethyl-pyridine (MEP), Hexylamino (HEA), Phenylpropylamino (PPA), 2-Mercapto-5-benzamidazole sulfo acid (MB I), Capto MMC (GEHC), N-benzyl-N-methyl ethanolamine (GEHC)), CHT hydroxyapatide and CHT fluoroapatide.

13. The method according to claim 12, wherein chromatography column is a column with a synthetic affinity ligand that is 4-mercapto-ethyl-pyridine (MEP).

14. The method of claim 2 further comprising an additional step of purifying the active beta-NGF.

15. The method of claim 14, wherein the active beta-NGF is purified by column chromatography.

16. The method of claim 15, wherein active beta-NGF is purified using a SP Sepharose HP column.

17. A method for preparing a biologically active human beta-NGF comprising:

providing a proNGF mutant wherein the protease cleavage site R1 SK3 R4 is substituted at least at positions R 1 and K 3 corresponding to positions 101 and 103 of the human wild type proNGF sequence (SEQ ID NO: 1) by an amino acid selected from the group consisting of a non-basic amino acid and Histidine; and cleaving the proNGF mutant to obtain active human beta-NGF.

18. The method of claim 17 further comprising the steps of:

dissolving the proNGF mutant wherein the protease cleavage site R1 SK3 R4 is substituted at least at positions R 1 and K 3 corresponding to positions 101 and 103 of the human wild type proNGF sequence (SEQ ID NO: 1) by an amino acid selected from the group consisting of a non-basic amino acid and Histidine by solubilization of inclusion bodies in a denaturing solution;

transferring the proNGF mutant into a refolding solution where the denatured proNGF assumes a biologically active conformation;

purifying the refolded proNGF mutant; and cleaving the pro-sequence of the proNGF mutant to obtain the active beta-NGF.

19. The method according to claim 17, wherein the pro-form of the proNGF mutant is cleaved by a protease.

20. The method according to claim 19, wherein the pro-form of the proNGF mutant is cleaved by a serine protease.

21. The method according to claim 20, wherein the pro-form of the proNGF mutant is cleaved by trypsin.

22. The method of claim 21, wherein the ratio of trypsin to proNGF mutant is from 1:200-1:100,000 (w/w).

23. The method of claim 22, wherein the ratio of trypsin to proNGF mutant is from 1:5,000-1:20,000 (w/w).

24. The mothod of claim 23, wherein the ratio of trypsin to proNGF mutant is form 1:10,000 (w/w).

25. A method for preparing a biologically active human beta-NGF comprising:

providing a proNGF mutant wherein the protease cleavage site R1 SK3 R4 is substituted at least at positions R 1 and K 3 corresponding to positions 101 and 103 of the human wild type proNGF sequence (SEQ ID NO: 1) by an amino acid selected from the group consisting of a non-basic amino acid and Histidine; and cleaving the pro-sequence of the proNGF mutant to obtain active human beta-NGF.

26. The method of claim 25 further comprising the steps of:

dissolving the proNGF mutant wherein the protease cleavage site R1 SK3 R4 is substituted at least at positions R 1 and K 3 corresponding to positions 101 and 103 of the human wild type proNGF sequence (SEQ ID NO: 1) by an amino acid selected from the group consisting of a non-basic amino acid and Histidine by solubilization of inclusion bodies in a denaturing solution;

transferring the proNGF mutant into a refolding solution where the denatured proNGF assumes a biologically active conformation; and purifying the refolded proNGF mutant.

* * * * *